(12) United States Patent
Tromberg et al.

(10) Patent No.: US 7,729,750 B2
(45) Date of Patent: Jun. 1, 2010

(54) METHOD AND APPARATUS FOR HIGH RESOLUTION SPATIALLY MODULATED FLUORESCENCE IMAGING AND TOMOGRAPHY

(75) Inventors: Bruce J. Tromberg, Irvine, CA (US); Anthony J. Durkin, Costa Mesa, CA (US); David Cuccia, Newport Beach, CA (US); Frederic Bevilacqua, Paris (FR)

(73) Assignee: The Regents of the University of California, Oakland, CA (US)

( * ) Notice: Subject to any disclaimer, the term of this patent is extended or adjusted under 35 U.S.C. 154(b) by 776 days.

(21) Appl. No.: 11/336,065

(22) Filed: Jan. 19, 2006

(65) Prior Publication Data
US 2006/0184043 A1 Aug. 17, 2006

(51) Int. Cl.
*A61B 6/00* (2006.01)
*G01J 3/42* (2006.01)
*G01J 3/30* (2006.01)

(52) U.S. Cl. ................ 600/476; 356/317; 356/318; 356/319

(58) Field of Classification Search ......... 600/473–479; 356/311–318
See application file for complete search history.

(56) References Cited

U.S. PATENT DOCUMENTS

| | | | |
|---|---|---|---|
| 5,865,754 A | 2/1999 | Sevick-Muraca et al. | |
| 6,122,042 A | 9/2000 | Wunderman et al. | |
| 6,208,886 B1 | 3/2001 | Alfano et al. | |
| 6,321,111 B1 | 11/2001 | Perelman et al. | |
| 6,405,069 B1 | 6/2002 | Oraevsky et al. | |
| 6,825,928 B2 | 11/2004 | Liu et al. | |
| 7,139,603 B2 * | 11/2006 | Chance | 600/473 |
| 7,274,446 B2 * | 9/2007 | Wolleschensky et al. | 356/300 |
| 2003/0184757 A1 | 10/2003 | Bevilcqua et al. | |
| 2004/0095576 A1 * | 5/2004 | Wolleschensky | 356/317 |

OTHER PUBLICATIONS

F. Bevilacqua, D. J. Cuccia, A. J. Durkin, and B. J. Tromberg, "Depth-sectioned subsurface imaging in turbid media using spatially modulated illumination," Frontiers in Optics, OSA Technical Digest, Optical Society of America, Tucson, Arizona Oct. 5, 2003.*
International Search Authority, International Search Report and Written Opinion dated Aug. 13, 2007, 13 pages.
International Bureau of WIPO, International Preliminary Report on Patentability dated Sep. 27, 2007, 11 pages.

* cited by examiner

*Primary Examiner*—Long V Le
*Assistant Examiner*—Angela M Hoffa
(74) *Attorney, Agent, or Firm*—Daniel L. Dawes; Marcus C. Dawes

(57) ABSTRACT

An improvement in a method for quantitative modulated imaging to perform depth sectioned reflectance or transmission imaging in a turbid medium, such as human or animal tissue is directed to the steps of encoding periodic pattern of illumination preferably with a fluorescent excitation wavelength when exposing a turbid medium to the periodic pattern to provide depth-resolved discrimination of structures within the turbid medium; and reconstructing a non-contact three dimensional image of the structure within a turbid medium. As a result, wide field imaging, separation of the average background optical properties from the heterogeneity components from a single image, separation of superficial features from deep features based on selection of spatial frequency of illumination, or qualitative and quantitative structure, function and composition information is extracted from spatially encoded data.

26 Claims, 17 Drawing Sheets

KNOWN "BULK" OPTICAL PROPERTIES:
$\mu_a = 0.00736/mm$

KNOWN "BULK" OPTICAL PROPERTIES:
$\mu_s' = 0.901/mm$

PRELIMINARY IN-VIVO FLUORESCENCE
EXPERIMENT: Cy5.5-LABLED WOUND-
TARGETING PEPTIDE*

METHOD AND APPARATUS FOR HIGH RESOLUTION SPATIALLY MODULATED FLUORESCENCE IMAGING AND TOMOGRAPHY

GOVERNMENT SUPPORT

This invention was made with Government support under Grant No. RR01192, awarded by the NIH. The Government has certain rights in this invention.

RELATED APPLICATIONS

The present application is related to U.S. Provisional Patent Application, Ser. No. 60/645,430, filed on Jan. 20, 2005, which is incorporated herein by reference and to which priority is claimed pursuant to 35 USC 119.

BACKGROUND OF THE INVENTION

1. Field of the Invention

The present invention relates to optical measurement of turbid media and in particular to optical measurement tissue absorption and scattering parameters and tissue imaging.

2. Description of the Prior Art

There is considerable prior art that utilizes structured illumination to carry out fluorescence based molecular imaging in small animals. The structured nature of the illumination, which is generally presented to the target at a single spatial frequency, is used in a very simple way to inform the spatial location and topography of the surface of the illuminated target to create a three dimensional rendering of the object. Essentially the approach is a method for correcting for variations in the distance between illumination to object and object to sensor. A number of examples follow.

For a first example, as described in "Visualization Of Antitumor Treatment By Means Of Fluorescence Molecular Tomography With A" Annexin V-Cy5.5 Conjugate" by Ntziachristos V, et. al. Proc Natl Acad Sci USA. 2004 Aug. 17; 101(33):12294-9. Epub 2004 Aug. 10 Center for Molecular Imaging Research, Massachusetts General Hospital and Harvard Medical School, Boston, Mass. 02115, USA. vasilis@helix.mgh.harvard.edu, in vivo imaging of treatment responses at the molecular level has been recognized as potentially having a significant impact on the speed of drug discovery and ultimately to personalized medicine. There is a recognized need for developing quantitative fluorescence-based technologies with good molecular specificity and sensitivity for noninvasive 3D imaging through tissues and whole animals. Tumor response to chemotherapy can be accurately resolved by fluorescence molecular tomography (FMT) with a phosphatidylserine-sensing fluorescent probe based on modified annexins. At least a 10-fold increase of fluorochrome concentration in cyclophosphamide-sensitive tumors and a 7-fold increase of resistant tumors compared with control studies has been observed. Fluorescence molecular tomography is an optical imaging technique developed to overcome limitations of commonly used planar illumination methods and demonstrates higher quantification accuracy validated by histology. A 3-fold variation in background absorption heterogeneity may yield 100% errors in planar imaging but only 20% error in fluorescence molecular tomography, thus confirming tomographic imaging as a preferred tool for quantitative investigations of fluorescent probes in tissues. Tomographic approaches are found essential for small-animal optical imaging and are potentially well suited for clinical drug development and monitoring."

For a second example as described in "In Vivo Tomographic Imaging Of Near-infrared Fluorescent Probes" by Ntziachristos V et. al., Mol Imaging. 2002 April-June; 1(2): 82-8. Center for Molecular Imaging Research, Massachusetts General Hospital & Harvard Medical School, Bldg. 149 13th Street 5406, Charlestown, Mass. 02129-2060, USA. vasilis@helix.mgh.harvard.edu, fluorescence imaging has increasingly been used to probe protein function and gene expression in live animals. This technology is seen in the art as enhancing the study of pathogenesis, drug development, and therapeutic intervention. Three-dimensional fluorescence observations using fluorescence-mediated molecular tomography (FMT) have been developed. An imaging technique that can resolve molecular function in deep tissues by reconstructing fluorescent probe distributions in vivo has been demonstrated. Fluorescence-mediated molecular tomography findings have been compared with fluorescence reflectance imaging (FRI) to study protease function in nude mice with subsurface implanted tumors. This validation of fluorescence-mediated molecular tomography with fluorescence reflectance imaging has demonstrated the spatial congruence of fluorochrome activation as determined by the two techniques.

For a third example as disclosed in "Experimental Fluorescence Tomography Of Tissues With Noncontact Measurements" by Schulz R B et. al. IEEE Trans Med Imaging. 2004 April; 23(4):492-500 Department of Medical Physics in Radiology, German Cancer Research Center (DKFZ), Im Neuenheimer Feld 280, 69120 Heidelberg, Germany. r.schulz@dkfz.de, noncontact optical measurements from diffuse media has been found to facilitate the use of large detector arrays at multiple angles in diffuse optical tomography applications. Such imaging strategy eliminates the need for individual fibers in contact with tissue, restricted geometries, and matching fluids. Thus, experimental procedures and the ability to visualize functional and molecular processes in vivo is improved as shown in an experimental implementation to perform small animal imaging.

Ultrasound can be used to access subsurface information to a certain degree; however this only gives data relating to tissue mechanical properties. Optical coherence tomography is currently being developed to probe tissue subsurface structure, but can only report on very small tissue volumes. Standard photography can be performed in such a way as to provide semiquantitative information relating to surface structure, but not subsurface structure.

Fluorescence tomography approaches until recently have been limited to arrays of single sources and detectors that are serially switched in order to build up a tomographic image of the object of interest. Typically these geometries are not accommodating to a wide variety of targets. Model based approaches are required in order to extract meaning from the data.

Recently there have been efforts that employ wide field imaging and structured illumination at a single spatial frequency in order to provide an estimate of the three dimensional extent of the target of interest. Much of this work has focused on small animal imaging. Investigators have relied on the spatial distortion of the projected static illumination pattern by the surface of the object in order to "correct" for sample-to-detector variation that results from the three dimensional extent of the object of interest.

U.S. Patent Application 2003/0184757 disclosed wide field, broadband, spatially modulated illumination of turbid media. This approach has potential for simultaneous surface and sub-surface mapping of media structure, function and composition. This method can be applied with no contact to the medium over a large area, and could be used in a variety of applications that require wide-field image characterization. Numerous potential applications in the biomedical domain were indicated including those utilizing fluorescence. While quantitative modulated fluorescence imaging was mentioned in passing, a detailed illustration was not provided.

BRIEF SUMMARY OF THE INVENTION

The illustrated embodiment of the invention is directed to a method for performing depth sectioned reflectance or transmission imaging in a turbid medium comprising the steps of: exposing the turbid medium to a periodic pattern of planar illumination at a plurality of spatial frequencies where the planar illumination corresponds to a fixed mean depth of data detection and where the plurality of spatial frequencies varies the depth sensitivity of data detection; receiving data images from the turbid medium for each of the plurality of spatial frequencies; selecting a region of interest of the turbid medium at a selected depth of the turbid medium; transforming the data image of the selected region of interest of the turbid medium at the selected depth; spatially filtering the transformed data image of the selected region of interest of the turbid medium at the selected depth; and reconstructing the filtered transformed data image of the selected region of interest of the turbid medium at the selected depth.

The illustrated embodiment of the invention also can be characterized as comprising the steps of: exposing the turbid medium to planar illumination at a spatially modulated frequency where the planar illumination corresponds to a fixed mean depth of data detection and where the spatial frequency corresponds to a depth sensitivity of data detection; measuring diffuse reflectance or transmission of the turbid medium as a selected frequency of spatial modulation of planar illumination; transforming the measured diffuse reflectance or transmission to obtain a diffuse reflectance or transmission spectrum; dividing the diffuse reflectance or transmission spectrum by a diffusion kernel to obtain a reconstructed object spectrum; and inverse transforming the reconstructed object spectrum to obtain reconstructed object data.

In this embodiment the step of dividing the diffuse reflectance or transmission spectrum by a diffusion kernel to obtain a reconstructed object spectrum comprises dividing the diffuse reflectance or transmission spectrum by a diffusion kernel using optical properties determined from multi-frequency optical property measurements of a background of the turbid medium in which objects of interest are included and known depth of the object of interest.

In one implementation the steps of transforming the measured diffuse reflectance or transmission to obtain a diffuse reflectance or transmission spectrum and inverse transforming the reconstructed object spectrum to obtain a reconstructed object image comprise Fourier transforming the measured diffuse reflectance or transmission to obtain a diffuse reflectance or transmission spectrum and inverse Fourier transforming the reconstructed object spectrum to obtain a reconstructed object image.

In other implementations the steps of transforming the measured diffuse reflectance or transmission to obtain a diffuse reflectance or transmission spectrum and inverse transforming the reconstructed object spectrum to obtain a reconstructed object image comprise Hilbert transforming or wavelet transforming the measured diffuse reflectance or transmission to obtain a diffuse reflectance or transmission spectrum, and inverse Hilbert transforming or inverse wavelet transforming respectively the reconstructed object spectrum to obtain a reconstructed object image.

In one embodiment the steps of measuring diffuse reflectance or transmission of the turbid medium as a selected frequency of spatial modulation of planar illumination; transforming the measured diffuse reflectance or transmission to obtain a diffuse reflectance or transmission spectrum; dividing the diffuse reflectance or transmission spectrum by a diffusion kernel to obtain a reconstructed object spectrum; and inverse transforming the reconstructed object spectrum to obtain a reconstructed object image comprises performing each step in two dimensions at the spatially modulated frequency corresponding to the fixed mean depth to obtain a two dimensional image of the object of interest in the turbid medium.

In this last embodiment each of the above steps of exposing, measuring, transforming, dividing, and inverse transforming are repeated at varying spatially modulated frequencies to obtain a plurality of images corresponding varying fixed mean depths; and subtraction images are generated from the plurality of images a corresponding varying fixed mean depths to obtain images substantially derived only from a corresponding single fixed mean depth in the turbid medium.

The step of measuring diffuse reflectance or transmission of the turbid medium as a selected frequency of spatial modulation of planar illumination comprises simultaneously measuring fluorescence, absorption and scattering of the planar illumination from the object of interest in the turbid medium at the corresponding depth. The step of simultaneously measuring comprises using a forward model of determining fluence rate as a function of depth and inverse techniques to obtain the fluorescence, absorption and scattering properties of the object of interest in the turbid medium at the corresponding depth. The step of using a forward model of determining fluence rate as a function of depth is given by $$\varphi_0(z) = 3P_0\left(\frac{\mu'_s}{\mu_{tr}}\right)\left(\frac{\mu'^2_{eff}}{\mu^2_{tr}} - 1\right)^{-1} \exp(-\mu_{tr}z) + C\exp(-\mu'_{eff}z)$$

where $\phi_0(z)$ is the fluence rate as a function of depth, z, $P_0$ is the incident optical power of the planar illumination, C is a constant determined by a choice of a boundary condition, $\mu'_s$ is the reduced scattering coefficient, $\mu_{tr}$ is the transport coefficient, and $\mu_{eff}$ is the effective scattering coefficient. The step of using inverse techniques to obtain the fluorescence, absorption and scattering properties of the object of interest comprises using a least-squares regression or pseudoinverse linear matrix multiplication.

An improvement in a method for quantitative modulated fluorescence imaging to perform depth sectioned fluorescence and reflectance imaging in a turbid medium, typically human or animal tissue. The method in which the improvement is made comprises exposing the turbid medium to a periodic pattern of illumination characterized by a spatial frequency; receiving the data image from the turbid medium; selecting a region of interest of the turbid medium; transforming the data image of the selected region of interest of the turbid medium; spatially filtering the transformed data image of the selected region of interest of the turbid medium; and reconstructing the filtered transformed data image of the selected region of interest of the turbid medium.

The improvement comprises encoding the periodic pattern of illumination with a fluorescent excitation wavelength when exposing the turbid medium to the periodic pattern to provide depth-resolved discrimination of fluorescent structures within the turbid medium; and reconstructing a noncontact three dimensional image of fluorescence within a turbid medium. As a result, wide field imaging, separation of the average background optical properties from the heterogeneity components from a single image, separation of superficial fluorescent features from deep fluorescent features based on selection of spatial frequency of illumination, or qualitative and quantitative structure, function and composition information is extracted from spatially encoded data.

The steps of encoding and reconstructing provides spatially resolved optical properties at the excitation and emission wavelengths of interest, and further comprising deconvolving the effects of scattering and absorption from the measured fluorescence.

The method further comprises the step of simultaneously mapping surface and subsurface media structure, function and composition. This is performed in a computer using the optical property maps at the reflection and emission frequencies and transformations of the same.

The method is performed as a wide field imaging technique without the use of fiber optics or other field of view restricting modalities. The step of wide field imaging comprises spatially resolving optical properties determination over a large area.

The method further comprises separating the average background optical properties from heterogeneity components from a single image.

The method further comprises separating superficial fluorescent features from deep fluorescent features based on selection of spatial frequency of illumination.

The method further comprises extracting qualitative and quantitative structure, function and composition information from spatially encoded data.

The step of simultaneously mapping surface and subsurface media structure, function and composition comprises assessing depth sensitivity as a function of source spatial frequency, wavelength selection and/or amplitude modulation.

The step of extracting qualitative and quantitative structure, function and composition information from spatially encoded data comprises quantitatively measuring fluorescence by both spatially resolving scattering and absorption properties in addition to fluorescence data and deconvolving the effects of scattering and absorption from fluorophore spectra. Again this is a data processing step performed in a computer according to the teachings of the invention.

The method further comprises the steps of separating background fluorescence from target fluorescence based on selection of spatial frequency of illumination, and separating superficial fluorescent features from deep fluorescent features based on selection of spatial frequency of illumination.

The method further comprises resolving in depth tissue auto fluorescence from other exogenous fluorophores or the expression of genetically engineered protein fluorescence within the tissue.

The method further comprises assessing depth sensitivity as a function of source spatial frequency, wavelength selection and/or amplitude modulation.

The method further comprises separating superficial fluorescent features from deep fluorescent features based on selection of spatial frequency of illumination.

In one embodiment the steps of encoding and reconstructing are applied to small animal imaging.

In various embodiments the steps of encoding and reconstructing are applied to at least one of pre-cancer and cancer detection and monitoring, using fluorescence endoscopy, fluorescence bronchosopy, fluorescence colposcopy (cervical cancer), intraoperative guidance for distinguishing between tissue types, Moh's surgery guidance (delineation of skin tumor margin based on fluorescence and/or reflectance), or brain tumor resection such a delineation of tumor margin based on fluorescence and/or reflectance.

In another embodiment the steps of encoding and reconstructing are applied to monitoring the efficacy of therapeutics such as in drug development.

In further embodiments the steps of encoding and reconstructing are applied to at least one of monitoring age, disease related changes, and cosmetic agents in skin, using wide field tissue hydration, photoaging and the response of photoaged skin to therapy (chemical, laser, radiofrequency or ablation), or quantification of the effectiveness of sunscreens (examination of both the sunscreen proper and physiologic response to radiation under different sunscreen formulations).

In still further embodiments the steps of encoding and reconstructing are applied to diabetes related changes in tissue status such fluorescence changes related to advanced glycation end products.

In yet another embodiment the steps of encoding and reconstructing are applied to burn severity/burn depth assessment for grafting.

In another embodiment the steps of encoding and reconstructing are applied to photodynamic therapy dosimetry.

In another embodiment the steps of encoding and reconstructing are applied to wide field tissue oximetry for burn assessment, peripheral vascular disease diagnosis and management, or neonatal oximetry.

In another embodiment the steps of encoding and reconstructing are applied to chemical imaging using fluorescence, reflectance or combination as means of quality control for pharmaceuticals and quantitative process engineering.

The illustrated embodiment of the invention also includes an improvement in an apparatus for quantitative modulated fluorescence imaging to perform depth sectioned fluorescence and reflectance imaging of a turbid sample, such as human or animal tissue. The turbid sample is also fluorescent either by means of the fluorescence of its natural constituents or by means of being infiltrated or combined with a fluorescent tag or dye. The apparatus in which the improvement is made comprises a source to expose a turbid sample to a periodic pattern of illumination; a camera to receive the data image from the sample; and a signal processor to Fourier transform the data image of the sample, to spatially filter the transformed data image of the sample, and to reconstruct the filtered transformed data image of the sample. The signal processor includes a software/firmware controlled computer, digital signal processor, logic circuits or any other signal processing circuit or device. The improvement is that the source provides the periodic pattern of illumination encoded with a fluorescent excitation wavelength to provide depth-resolved discrimination of fluorescent structures within the turbid medium. The apparatus is combined with a means for reconstructing a non-contact three dimensional image of fluorescence at an emission frequency within the turbid sample. This may be the signal processor of the apparatus or may be an additional software/firmware controlled computer, digital signal processor, logic circuits or any other signal processing circuit or device. As a result wide field imaging, separation of the average background optical properties from the heterogeneity components from a single image, separation of superficial fluorescent features from deep fluorescent features based on selection of spatial frequency of illumination, or qualitative and quantitative structure, function and composition information is extracted from spatially encoded data.

The source and means for reconstructing in combination determine spatially resolved optical properties at the excitation and emission wavelengths of interest, and the means for reconstructing further deconvolving the effects of scattering and absorption from the measured fluorescence.

The means for reconstructing further simultaneously maps surface and subsurface media structure, function and composition.

The source and means for reconstructing in combination perform wide field imaging.

The means for reconstructing separates the average background optical properties from heterogeneity components from a single image.

The means for reconstructing separates superficial fluorescent features from deep fluorescent features based on selection of spatial frequency of illumination.

The means for reconstructing extracts qualitative and quantitative structure, function and composition information from spatially encoded data.

The means for reconstructing assesses depth sensitivity as a function of source spatial frequency, wavelength selection and/or amplitude modulation.

The means for reconstructing spatially resolves optical properties determination over a large area.

The means for reconstructing quantitatively measures fluorescence by both spatially resolving scattering and absorption properties in addition to fluorescence data and deconvolving the effects of scattering and absorption from fluorophore spectra.

The means for reconstructing separates background fluorescence from target fluorescence based on selection of spatial frequency of illumination, and separates superficial fluorescent features from deep fluorescent features based on selection of spatial frequency of illumination.

The means for reconstructing resolves in depth tissue auto fluorescence from other exogenous fluorophores or the expression of genetically engineered protein fluorescence within the tissue.

The means for reconstructing assesses depth sensitivity as a function of source spatial frequency, wavelength selection and/or amplitude modulation.

The means for reconstructing separates superficial fluorescent features from deep fluorescent features based on selection of spatial frequency of illumination.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1b is a side diagrammatic view of the phantom of FIG. 1a.

FIG. 18 also shows in the leftmost portion a photograph of the diffuse reflectance image measured for a planar illumination (spatial frequency=0/mm). In the center portion is a graph of the spatial profiles of absorbing perturbation at each of 42 spatial frequencies ranging from 0/mm to 0.5/mm. At the rightmost portion is the normalized perturbation profiles indicate a changing sensitivity to the absorbing object with increasing spatial frequency due to the changing depth-resolved background fluence profile.

Figure 1A:
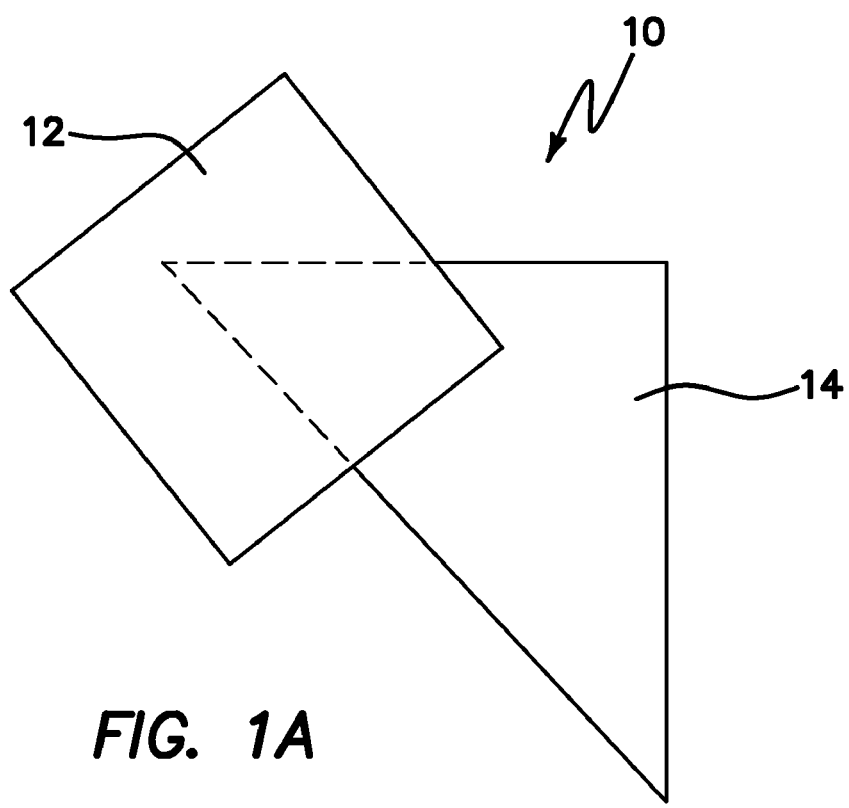
FIG. 1a is a diagrammatic top plan view of a first phantom.

discussed below, and tomographic inversion techniques such as least-squares regression or pseudoinverse linear matrix multiplication.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Illumination with a pattern of light allows for subsurface imaging of a turbid medium or tissue, and for the determination of the optical properties over a large area. Both the average and the spatial variation of the optical properties can be noninvasively determined. Contact with the sample or scanning is not required but may be desired. Subsurface imaging is performed by filtering the spectrum of the illumination in the Fourier domain but other filtering approaches, such as wavelet transform, principle component filter, etc may be viable as well. The depth sensitivity is optimized by changing the spatial frequency of illumination. A quantitative analysis of the average optical properties and the spatial variation of the optical properties is obtained. The optical properties, i.e. reduced scattering and absorption coefficients are determined from the modulated transfer function, MTF., which is incorporated herein by reference, disclosed wide field, broadband, spatially modulated illumination of turbid media. Here we provide further improvements to the method and apparatus, namely modulated imaging.

In addition we provide a description of the information content that may be deduced from a fluorescence oriented application of the technique. Objects of the invention include means to perform 1) depth sectioned fluorescence and reflectance imaging in turbid media, and 2) deduction of spatially resolved fluorescence and optical properties. This approach can provide simultaneous surface and subsurface mapping of media structure, function and composition. The method disclosed herein allows wide field imaging; and separation of the average background optical properties from the heterogeneity components from a single image. In addition it provides a means for separation of superficial fluorescent features from deep fluorescent features based on selection of spatial frequency of illumination. Qualitative and quantitative structure, function and composition information can be extracted from spatially encoded data.

In the present method and apparatus for spatially modulated fluorescence imaging and tomography, the light distribution introduced into a turbid medium is encoded by the spatial frequency of the illumination, via modulated imaging, thereby allowing depth-resolved discrimination of fluorescent structures within a turbid medium. This enables a simple, non-contact three dimensional reconstruction of fluorescence within a turbid medium.

Furthermore, because the technique has the capacity to provide spatially resolved optical properties at the excitation and emission wavelengths of interest, one can use this approach to deconvolve the effects of scattering and absorption from the measured fluorescence (which can be endogenous, exogenous or a combination of the two).

This approach has potential for simultaneous surface and subsurface mapping of media structure, function and composition. The disclosed method allows wide field imaging; and separation of the average background optical properties from the heterogeneity components from a single image. In addition it provides a means for separation of superficial fluorescent features from deep fluorescent features based on selection of spatial frequency of illumination. Qualitative and quantitative structure, function and composition information can be extracted from spatially encoded data.

Figure 13:
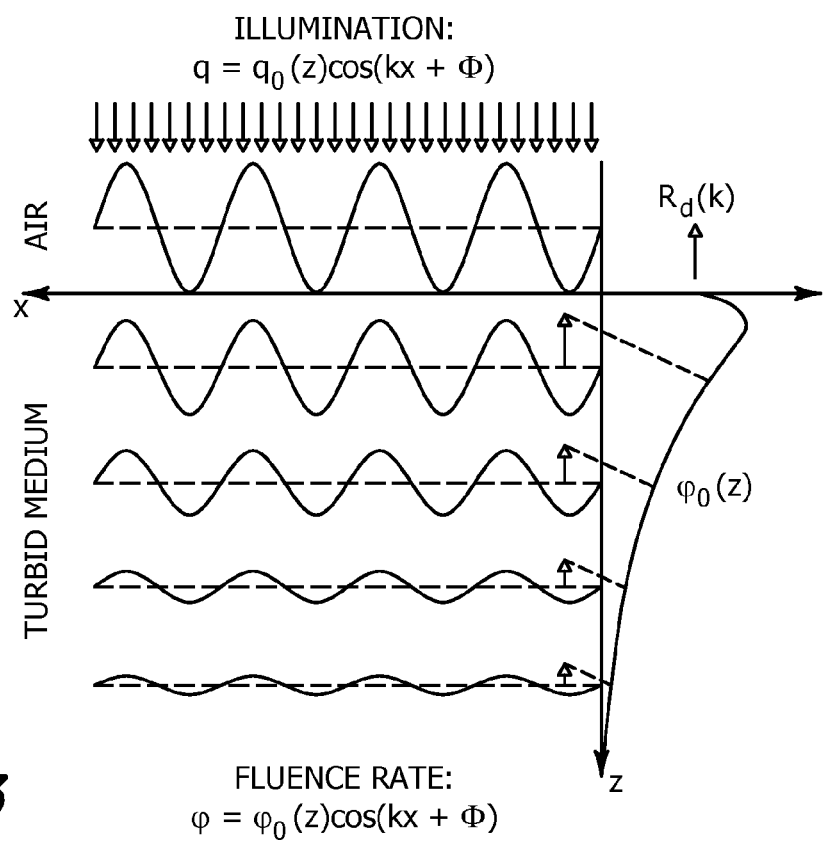
FIG. 13 is a diagram symbolically depicting a modulated illumination source and the resulting modulated internal fluence rate in a turbid medium, which includes tissue.

Theory in the Spatial Frequency Domain:

The time-independent form of the diffusion equation for a homogeneous medium is given by $$\nabla^2 \phi - \mu_{eff}^2 \phi = -3\mu_{tr} q, \quad (1)$$

where $\phi$ is the fluence rate, q is the source, $\mu_{tr} = \mu_a + \mu_s'$ is the transport coefficient, $\mu_{eff} = (3\mu_a \mu_{tr})^{1/2}$, $\mu_a$ is the absorption coefficient, $\mu_s' = \mu_s(1-g)$ is the reduced scattering coefficient, and g is the cosine of the average scattering angle. Imposing a semi-infinite geometry, as in FIG. 13, we introduce a normally-incident, periodically-varying plane wave source, $$q = q_0(z)\cos(kx + \Phi), \quad (2)$$

with spatial frequency (or repetency) $f_x = k/2\pi$ and spatial phase $\Phi$, extending infinitely in the tangential spatial dimension, x, with some arbitrary dependence on depth, z. As the light propagates into the medium, it is scattered equally in the positive and negative x directions, attenuating the AC wave amplitude. Assuming a linear medium, this sinusoid source gives rise to a fluence rate with the same oscillatory behavior in x (i.e. there is no lateral phase shift for normally incident light):

$$\phi = \phi_0(z)\cos(kx + \Phi). \quad (3)$$

Inserting Equations 2 and 3 into Equation 1 gives rise to a one dimensional second-order Helmholtz equation on fluence rate in depth, z:

$$\frac{d^2}{dz^2}\varphi_0(z) - \mu_{eff}'^2 \varphi_0(z) = -3\mu_{tr} q_0(z), \quad (4)$$

where $$\mu_{eff}' = (\mu_{eff}^2 + k^2)^{1/2} = \frac{1}{\delta_{eff}'}. \quad (5)$$

At zero spatial frequency (k=0), the effective penetration depth $\delta_{eff}'$ is equivalent to that of a planar illumination source, $\delta_{eff}' = 1/\mu_{eff}$. In general, however, $\mu_{eff}'$ and $\delta_{eff}'$ are functions of the both the optical properties and the spatial frequency of illumination. The one-dimensional form of Equation 4 implies that the amplitude of the periodic wave, $\phi_0(z)$, has no true dependence on the lateral dimension x. As Equation 4 is identical to the diffusion equation for a planar illumination, we can use existing planar geometry solutions by simply substituting $\mu_{eff}$ with our new $\mu_{eff}'$ term.

Following a standard derivation for planar photon density wave reflectance, we model an extended source $$q_0(z) = P_0 \mu_s' \exp(-\mu_{tr} z), \tag{6}$$

and arrive at a representation for the fluence rate $$\varphi_0(z) = 3P_0 \left(\frac{\mu_s'}{\mu_{tr}}\right)\left(\frac{\mu_{eff}'^2}{\mu_{tr}^2} - 1\right)^{-1} \exp(-\mu_{tr} z) + C\exp(-\mu_{eff}' z) \tag{7}$$

Here, $P_0$ is the incident optical power, and C is a constant determined by the choice of a boundary condition. Using the partial current boundary condition where the flux, j, is set proportional to the fluence at the interface z=0:

$$j|_{z \to 0^+} = A\varphi|_{z \to 0^+}; A = \frac{1 - R_{eff}}{2(1 + R_{eff})}, \tag{8}$$

with effective reflection coefficient $R_{eff}$ $$R_{eff} \approx 0.0636n + 0.668 + \frac{0.710}{n} - \frac{1.440}{n^2}, \tag{9}$$

we arrive at the diffuse reflectance, $R_d(k)$:

$$R_d(k) = \frac{3Aa'}{(\mu_{eff}'/\mu_{tr} + 1)(\mu_{eff}'/\mu_{tr} + 3A)}; a' = \frac{\mu_s'}{\mu_{tr}}; \tag{10}$$

where a' is the reduced albedo. While the formulation shown is for a pure one dimensional sinusoidal illumination pattern, an arbitrary illumination function can be modeled through linear superposition of sinusoids in two directions.

There are two major implications of Equations 7 and 10. First, varying the spatial frequency of the illumination pattern allows one to control the depth sensitivity of detection inside the turbid medium, whereas using planar illumination corresponds to fixed mean depth of interrogation. Second, by analyzing the frequency-dependent reflectance, one can quantitatively sample the optical properties of the medium. This is analogous to the frequency-domain photon migration approach, where time and spatial frequency measurements are each related by a Fourier transformation to time-resolved and spatially-resolved measurements, respectively.

While we formulate these concepts within a diffusion context, they are qualitatively retained in more accurate solutions to the full radiative transport equation, such as stochastic Monte Carlo simulations or direct numerical solutions, which extend light transport models to low scattering, high absorption, and/or high spatial frequency regimes.

Measurement in the Spatial Frequency Domain:

The diffuse modulation transfer function (MTF) of a turbid system can be measured in a transmission or reflection geometry. In practice, the illumination must be a superposition of AC (spatially-modulated) and DC (planar) reflectance terms inasmuch as it is physically impossible to illuminate with a negative scalar intensity. We therefore illuminate the sample with a spatial pattern of the form:

$$S = \frac{S_0}{2}[1 + M_0 \cos(2\pi f_x x + \Phi)], \tag{17}$$

where $S_0$, $M_0$, $f_x$, and $\Phi$ are the illumination source intensity, modulation depth, spatial frequency, and spatial phase, respectively. In this simple case, the pattern is constant in the orthogonal y-direction. In reflection mode the diffusely-reflected intensity, I, is a sum of AC and DC components:

$$I = I_{AC} + I_{DC}, \tag{18}$$

where the measured AC component of the reflected intensity, $I_{AC}$, can be modeled as:

$$I_{AC} = M_{AC}(x, f_x) * \cos(2\pi f_x x + \Phi). \tag{19}$$

Figure 14:
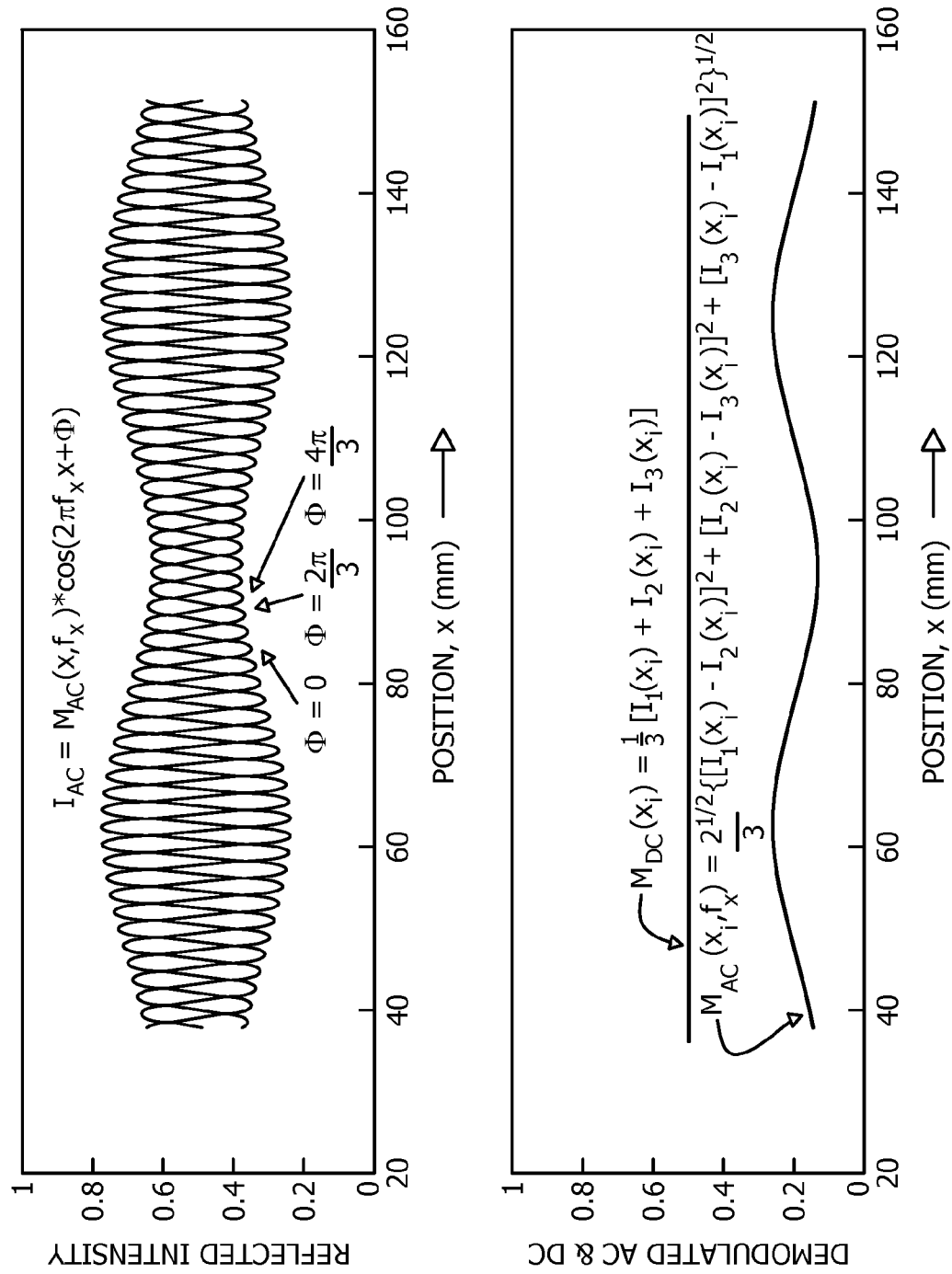
FIG. 14 is a graph of the modulated reflectance as shown in the upper portion, and demodulated AC and DC amplitudes as shown in the lower portion of the drawing.

Here, $M_{AC}(x, f_x)$ represents the amplitude of the reflected photon density "standing wave" at frequency $f_x$. Note first that a $M_{AC}$ can be a function of position, x, shown in the upper portion of FIG. 14. Additionally, multiple $M_{AC}(x, f_x)$ curves can be sampled in parallel at each y pixel row using a two dimensional camera, allowing spatial sampling of millions of reflectance values simultaneously.

Any one of a large number of conventional signal processing schemes can be used to obtain $M_{AC}(x, f_x)$. In the illustrated embodiment, we employ a simple time domain amplitude demodulation method, illuminating a sinusoid pattern three times at the same spatial frequency, with phase offsets $\Phi=0$, $\frac{2}{3}\pi$ and $\frac{4}{3}\pi$ radians. $M_{AC}(x, f_x)$ can then be calculated algebraically at each spatial location, $x_i$, by:

$$M_{AC}(x_i, f_x) = \tag{20}$$
$$\frac{2^{1/2}}{3}\{[I_1(x_i) - I_2(x_i)]^2 + [I_2(x_i) - I_3(x_i)]^2 + [I_3(x_i) - I_1(x_i)]^2\}^{1/2}$$

where $I_1$, $I_2$, and $I_3$ represent the $I_{AC}$ image values at each location with shifted spatial phases. This differencing approach is convenient as it: 1) automatically removes features common to all three images, including the average image noise and digitization offset; and 2) doesn't require knowledge of the spatial frequency, removing potential spatial calibration errors. The spatially-varying DC amplitude, $M_{DC}(X)$, can be calculated as above with $f_x=0$, or at any frequency of illumination using:

$$M_{DC}(x_i) = \frac{1}{3}[I_1(x_i) + I_2(x_i) + I_3(x_i)] \tag{21}$$

Note here that the above phase-shifting time-domain method for demodulation is only one of many different conventional approaches which all server the same purpose, namely to calculate the spatially-localized amplitude of the spatially varying diffuse photon density wave. Other time-domain and frequency-domain signal processing methods for demodulation include Hilbert transformation, wavelet transformation, and a Fourier transformation→division→based filtering→inverse Fourier transformation method.

In the frequency domain, a measurement $M_{AC}(f_x)$ is the product of: 1) the source intensity, $I_0$; 2) the MTF of the illumination and imaging optical system, $MTF_{system}$; and 3) the true turbid system MTF, $R_d$:

$$M_{AC}(x_i,f_x)=I_0 \cdot MTF_{system}(x_i,f_x) \cdot R_d(x_i,f_x) \quad (22)$$

Therefore, we can simultaneously calibrate for the absolute intensity of the source and the MTF of the imaging system by performing a reference measurement, $M_{AC,ref}(x,f_x)$, on a turbid phantom of known optical properties. Using a model prediction for the phantom diffuse reflectance, $R_{d,ref,pred}(f_x)$, we can write the diffuse reflectance at each spatial location as:

$$R_d(x_i, f_x) = \frac{M_{AC}(x_i, f_x)}{M_{AC,ref}(x_i, f_x)} \cdot R_{d,ref,pred}(f_x) \quad (23)$$

This direct division-based correction for the system frequency response is an advantage of spectral Fourier domain (SFD) measurement over other spatially-resolved measurements, avoiding system point spread function (PSF) deconvolution in the real spatial domain which can amplify measurement noise and uncertainties.

Finally, for a given modulation frequency, there are two unknowns in Equation 10, namely $\mu_a$ and $\mu_s'$. Therefore, measurements at as few as two spatial frequencies of can be used to separate absorption and scattering. In the illustrated embodiment, we use a "sweep" in spatial frequency space, analogous to the broadband frequency domain photon migration (FDPM) approach, producing an over determined set of measurements which can be fit to Equation 10 using least-squares minimization.

Figure 1B:
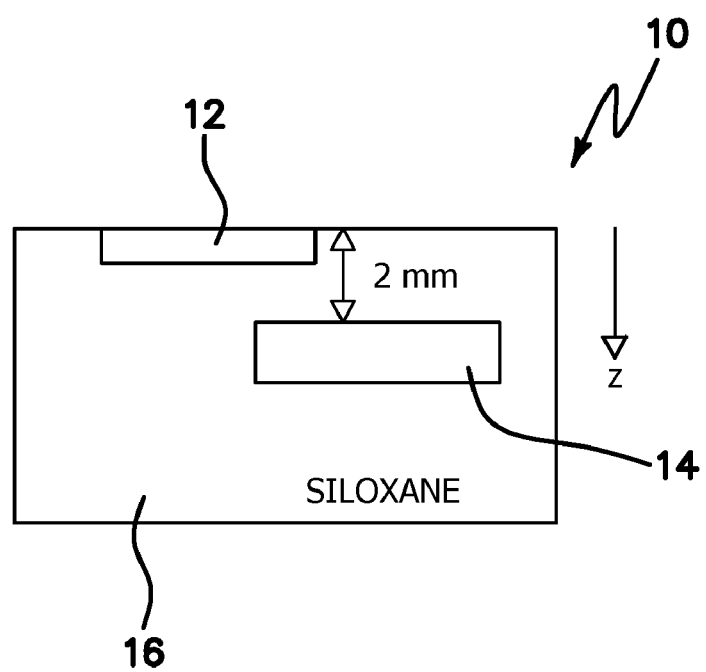
Figure 12:
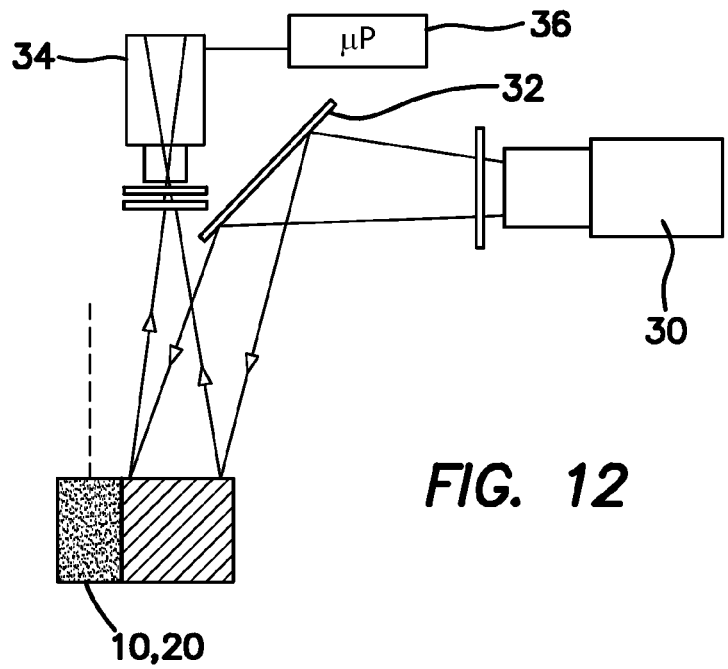
FIG. 12 is a diagram of an experimental setup in which the above images are provided.

As diagrammatically depicted in FIGS. 1a and 1b, which illustrate the phantom 10 experimental data have been acquired using a digital projector 30 employing a digital micromirror device 32 for illumination in a system diagrammatically depicted in FIG. 12 and described in detail in incorporated U.S. Pat. No. 6,958,815. Sinusoid patterns of various spatial frequencies are projected onto a heterogeneous phantom 10 and are captured by a Peltier-cooled 16-bit CCD camera 34. Data is taken from camera 34 and input into a computer 36.

Phantom 10 as shown in the top plan view of FIG. 1a is comprised of a square scattering and absorbing object 12 positioned above and offset from a triangular absorbing object 14, both of which are immersed in a block 16 of $TiO_2$ loaded siloxane. Phantom 10 is shown in side view in FIG. 1b where the upper surface of square scattering and absorbing material 12 is disposed 2 mm above triangular absorbing material 14. Siloxane block 16 was modified to contain $TiO_2$ ($\mu_a$=0.003/mm, $\mu_s'$=1/mm at 640 nm) and accommodated the two heterogeneities or objects 12 and 14. Object 14 was an absorbing mask (triangular in shape) was placed 2 mm inside the sample. Object 12 was a scattering and absorbing element (square in shape) placed at the surface of the siloxane block (thickness=0.5 mm, $\mu_a$=0.006/mm, $\mu_s'$=1/mm).

The specular reflection is carefully avoided by illuminating phantom 10 at a small angle relative to the normal direction, and by using crossed linear polarizers. Interference filters allow selection of a narrow wavelength band ($\lambda$=640 nm, $\Delta\lambda$=20 nm full width at half maximum, in the examples shown here). A siloxane reflectance standard is used to calibrate the measured intensity and to correct for spatial nonuniformity in both the illumination and imaging systems.

In practice, the illumination is in the form $M^*\cos(2\pi f_x + \phi)+1$, containing a DC (planar) component to allow for modulation from 0 to 1. In order to view the reflectance due to the AC and DC components separately, a conventional technique in signal processing is employed. This requires illuminating the sample three times at the same spatial frequency with phase offsets of 0, 120 and 240 degrees. An image of the AC modulated reflectance can be calculated using Eq (5), $$AC = \frac{\sqrt{3}}{2}\sqrt{(A-B)^2+(B-C)^2+(C-A)^2} \quad (5)$$

where A, B, and C represent the reflectance images with shifted spatial phases. This method has been recently employed in the art for use in confocal microscopy.

Figure 2:
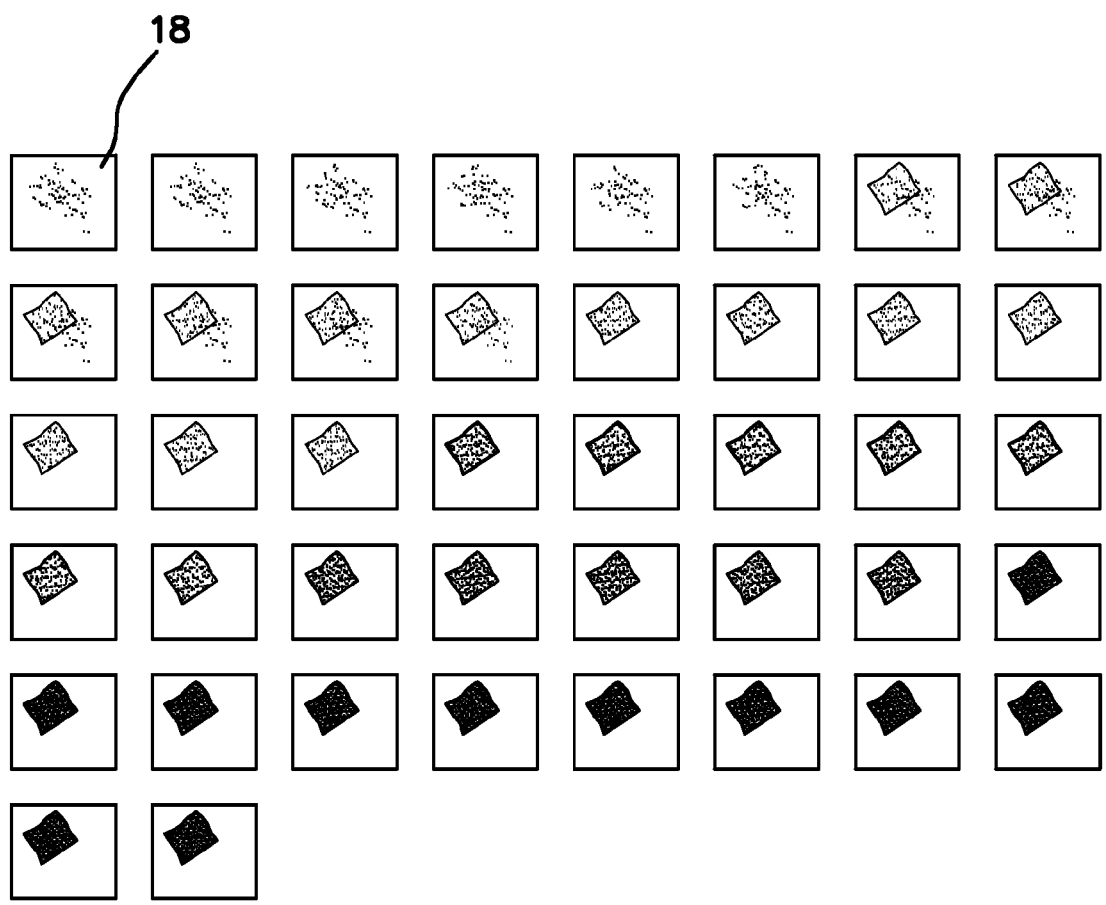
FIG. 2 is an array of data photographs showing phantom modulation images at 42 spatial frequencies.

FIG. 2 demonstrates that the effective contrast of the different objects 12 ad 14 depends on the spatial frequency of the illumination. FIG. 2 is an array of two dimensional data photographs showing phantom modulation images at 42 spatial frequencies. Starting at top left of FIG. 2, the spatial frequency used for the modulation images increases to the right and down from 0/mm (DC) to 0.63/mm. In the DC image 18, both superficial and deep objects appear. However, as the spatial frequency of illumination increases (to the right and down), the lower object becomes decreasingly apparent, until finally only the superficial object is visible. This is consistent with our formulation that high-frequency photon density waves penetrate only superficially.

Figure 3:
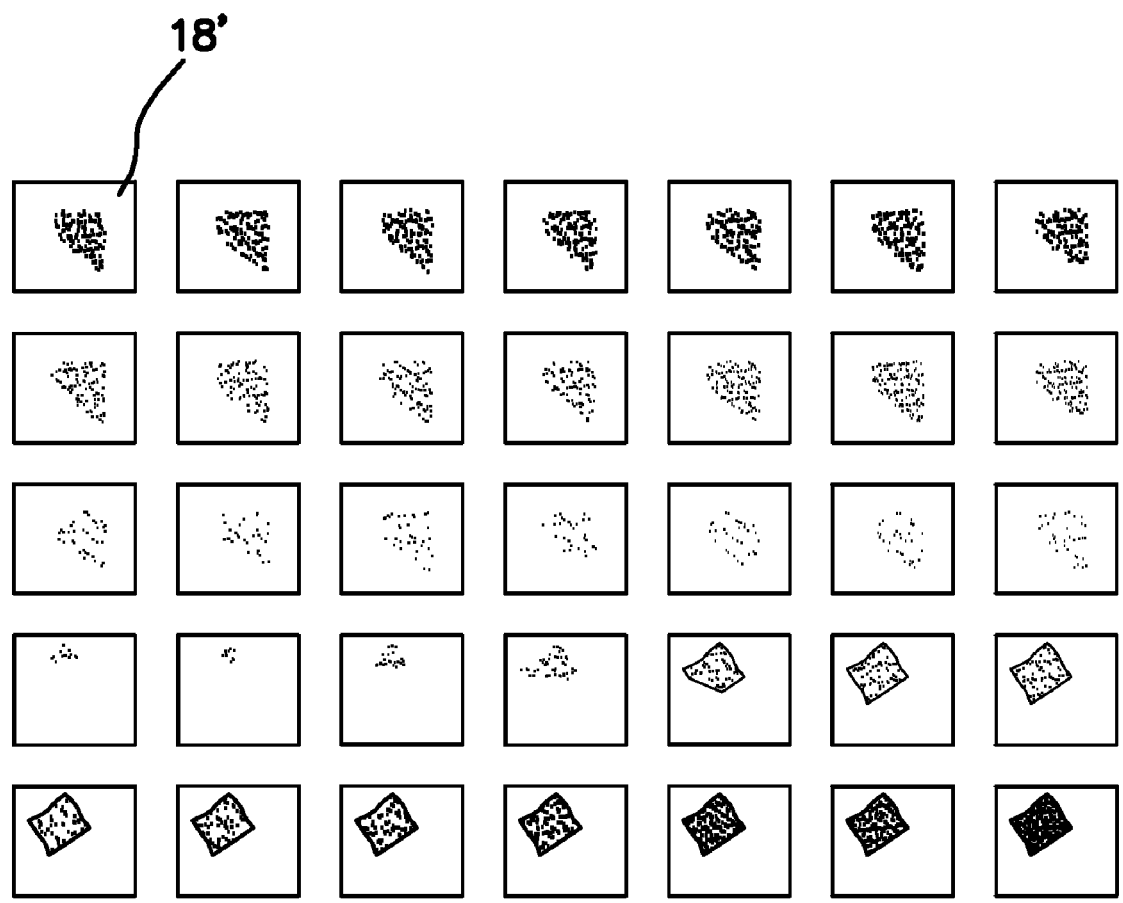
FIG. 3 is an array of data photographs which are difference images derived from the array of data photographs of FIG. 2.

Encoded in the data of FIG. 2 are the depth-resolved optical properties. A range of available quantitative tomographic reconstruction techniques for turbid media can be applied toward solving the spatially-heterogeneous inverse problem in 3D. Nevertheless, simple difference images between two neighboring spatial frequencies allow visualization of the information content changing with spatial frequency. Shown in FIG. 3 are difference images of the data set in FIG. 2. FIG. 3 is an array of depth-sectioned tomographs corresponding to the array of data photographs of FIG. 2 data by simple subtraction between modulation images at different spatial frequencies. Here, each of the 35 images is a result of subtraction between data in a moving frequency window (f1-f9, f2-f10, etc....) to capture bulk changes in depth sensitivity. In each image of FIG. 3, pixel values are plotted between 0.5 and 1.5 times the individual image mean value in order to allow a fair comparison of images across frequency space. This simple reconstruction reveals the lower object 14 and upper object 12 exclusively at low and high frequencies respectively, demonstrating the depth-resolving power of this technique.

Figure 4:
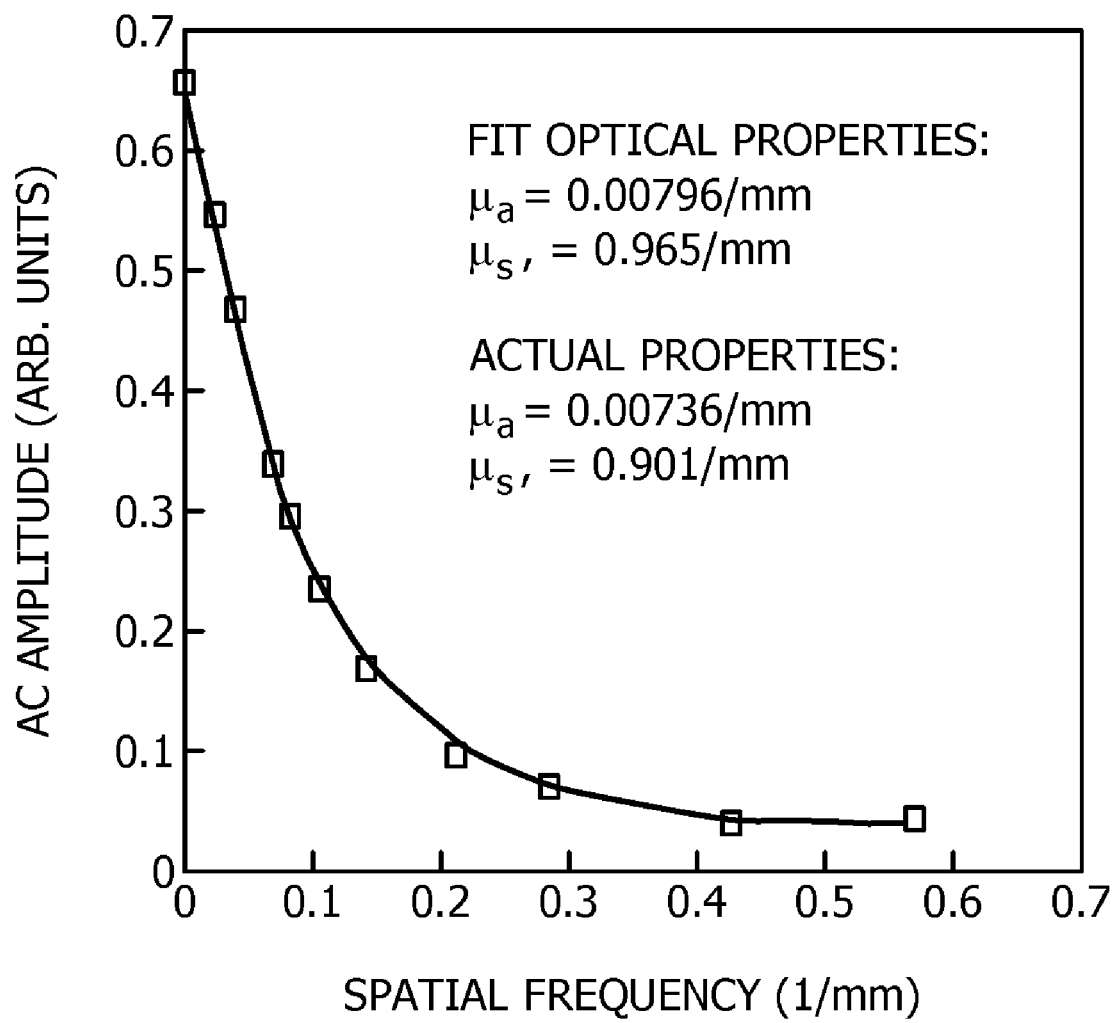
FIG. 4 is a graph of multi-frequency data, AC amplitude, shown in the boxes, and the corresponding fit, shown as a solid line, as a function of spatial frequency.

Optical Property Mapping Example—Homogeneous Phantom:

The second set of experiments imaged siloxane phantoms that were designed to be homogeneous. FIG. 4 is a graph of multi-frequency data, shown in the boxes, and the corresponding fit, shown as a solid line. The turbid medium acts as a low-pass filter. The known 'bulk' optical properties at 640 nm were: $\mu_a$=0.00736/mm, $\mu_s'$=0.901/mm, as measured by large source-detector separation frequency domain photon migration (FDPM). Eleven, 3-image sets were acquired over a 5×5 $cm^2$ surface, with spatial frequencies ranging from 0/mm to 0.6/mm. Modulation images at each frequency were obtained as previously described. The resulting 11 images provide a quantitative 'frequency-response', or modulation transfer function (MTF) of the diffuse reflectance of the turbid phantom. Moreover, this MTF is available at each pixel. Diffuse reflectance vs. frequency can be predicted analytically by taking a spatial Fourier transform of a spatially-resolved reflectance model. This enables phantom-based calibration and least-squares regression to obtain the absolute optical properties of the sample. Here, phantom calibration accounts for both the lamp intensity and MTF of the imaging optics.

Example MTF data are shown in FIG. 4 as identified by the points graphed as unfilled boxes. Each data point represents an average over the entire modulation image. Notice that the tissue sample acts like a low-pass filter, attenuating the reflectance more strongly as spatial frequency increases. These data were fit to an analytical diffuse reflectance model using a non-linear least-squares optimization routine. The recovered optical properties were $\mu_a$=0.00796/mm, $\mu_s'$=0.965/mm, very close to the known 'bulk' values of $\mu_a$=0.00736/mm, $\mu_s'$=0.901/mm.

Figure 5:
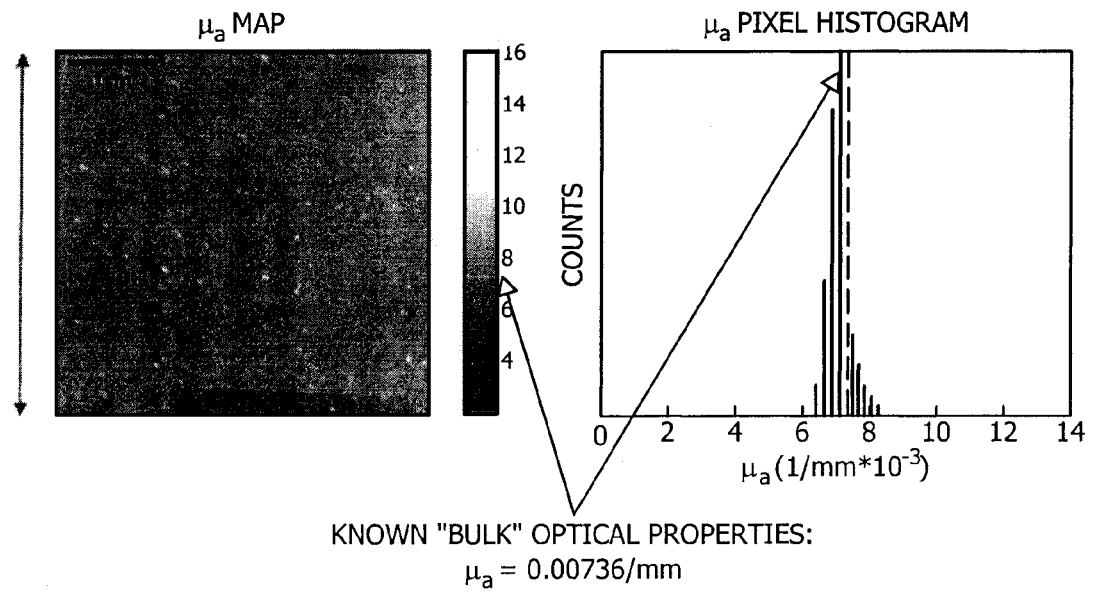
FIG. 5 is a two dimensional data map of the recovered absorption properties $\mu_a$ and scattering properties $\mu_{s'}$ on the upper and lower left sides respectively with corresponding pixel histograms on the upper and lower right sides respectively.
Figure 5:
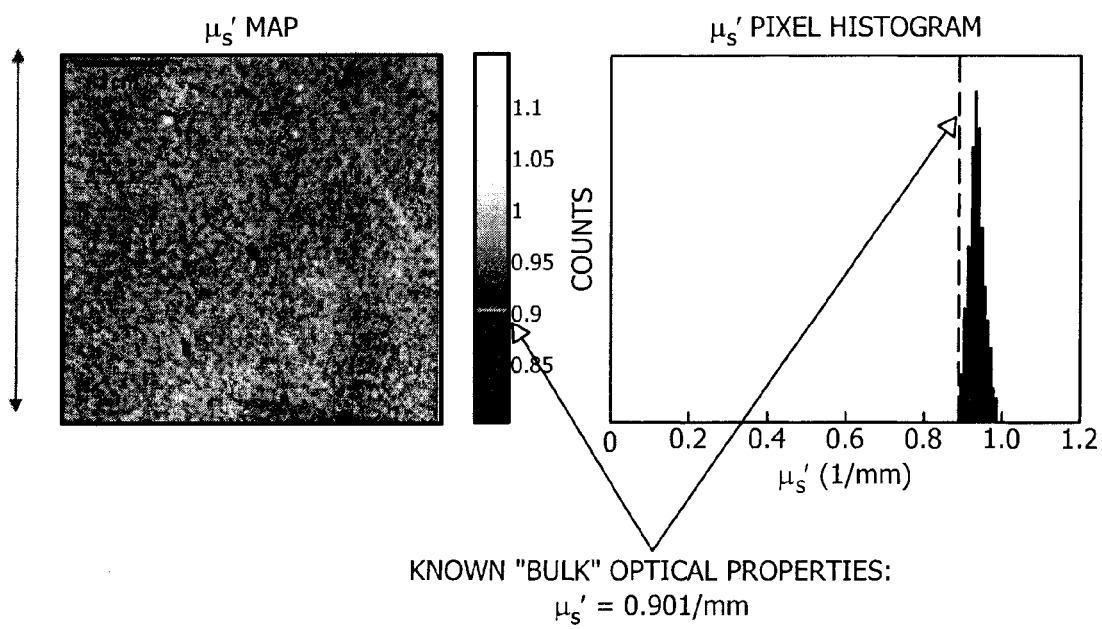

Because the AC modulation is determined at each pixel, it is possible to do a pixel-by-pixel frequency fit. This was performed over the 5×5 cm$^2$ area (approx. 500×500 pixels). Two dimensional data maps of the recovered absorption properties $\mu_a$ and scattering properties $\mu_s'$ are shown in FIG. 5. To the right of each map is a histogram of pixel values, with a black dotted line indicating the known bulk values of $\mu_a$=0.00736/mm, $\mu_s'$=0.901/mm. The recovered properties are in very good agreement to the known bulk properties, with the bulk properties falling well within the corresponding histograms. This is especially exciting as the known bulk properties were determined from large source-detector separation FDPM measurements. This demonstrates the power of the invention to return the optical properties of the illuminated sample.

Figure 6:
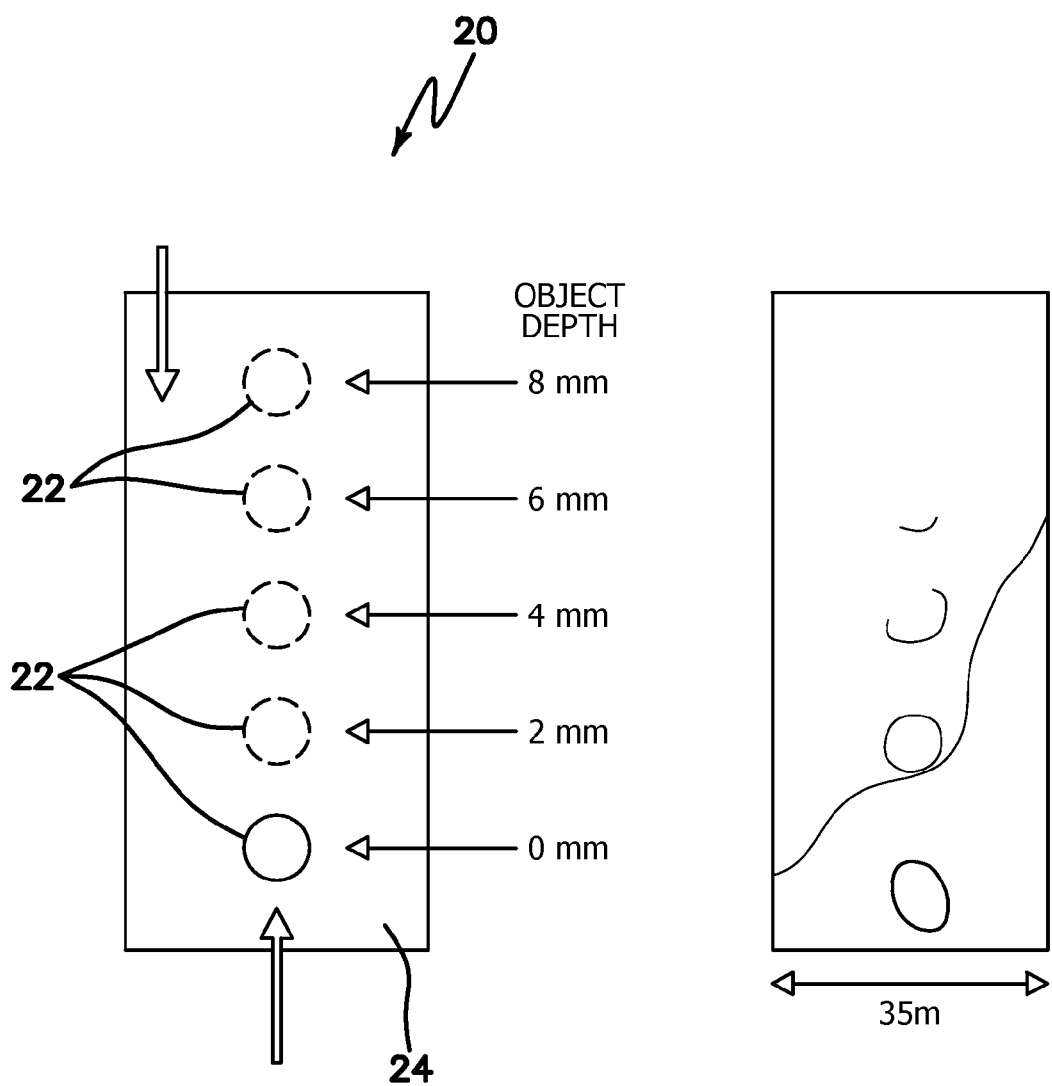
FIG. 6 is a diagrammatic depiction of a second depth phantom on the left side with its corresponding reflection depth image on the right side.

Turn now to a heterogeneous phantom experiment wherein depth-dependent fluorescence imaging is demonstrated. This experiment was performed to validate that the same type of depth-sectioning and tomography is possible for fluorescence as for reflectance/absorbance/scattering shown earlier. To this end as shown on the left side of FIG. 6, a solid siloxane phantom 20 was constructed with five cylindrical, liquid perturbations 22 embedded in siloxane 24 in fluorescence (100 nM:1 nM perturbation:background) fluorescence at various depths, ranging from the surface to as deep as 8 mm. Phantom 20 provided a homogeneous background with $\mu_a$=0.0016/mm, $\mu_s'$=1.3/mm and with a fluorescence: 1 nM Cy5.5 dye. Fluorescence excitation was at 660 nm, and DC reflection data was collected at both the excitation (pass-through) and emission bands (720 nm bandpass filter). DC reflection data at 660 nm±10 nm is shown to the right in FIG. 6.

Figure 7:
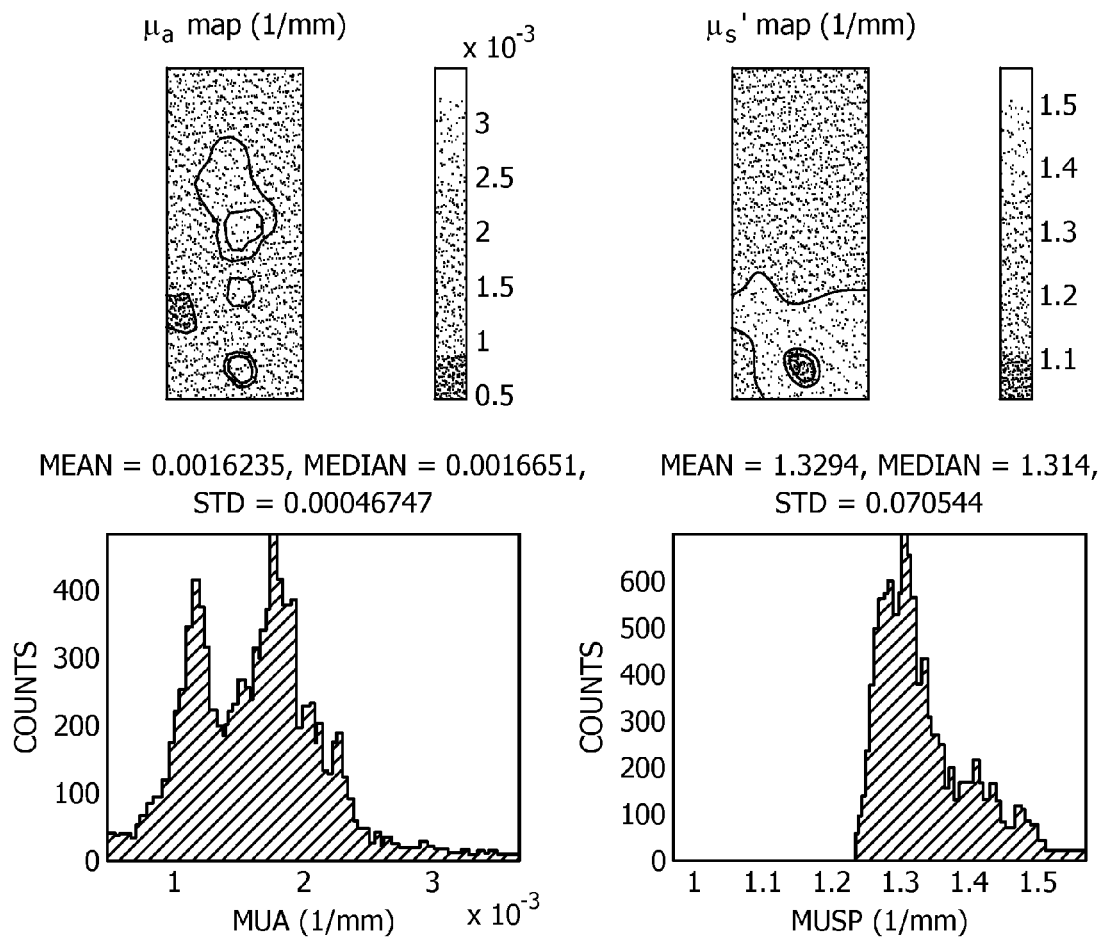
FIG. 7 shows in the upper portion excitation optical property maps, namely $\mu_a$ and $\mu_{s'}$ data maps, at 660 nm of the phantom of FIG. 6. The lower portion of FIG. 7 are corresponding quantitative histograms for $\mu_a$ and $\mu_{s'}$.

Excitation optical property maps, namely $\mu_a$ and $\mu_s'$ data maps, at 660 nm are shown in the upper portion of FIG. 7. The lower portion of FIG. 7 are corresponding quantitative histograms for $\mu_a$ and $\mu_s'$. The optical property maps at the excitation wavelength appear as expected. The measured absorption is clearly higher for areas over the perturbation. The reduced scattering is lower, possibly due to the change in refractive index of liquid and solid phantoms. The absorption becomes weaker and more diffuse as the perturbation gets deeper.

Figure 8:
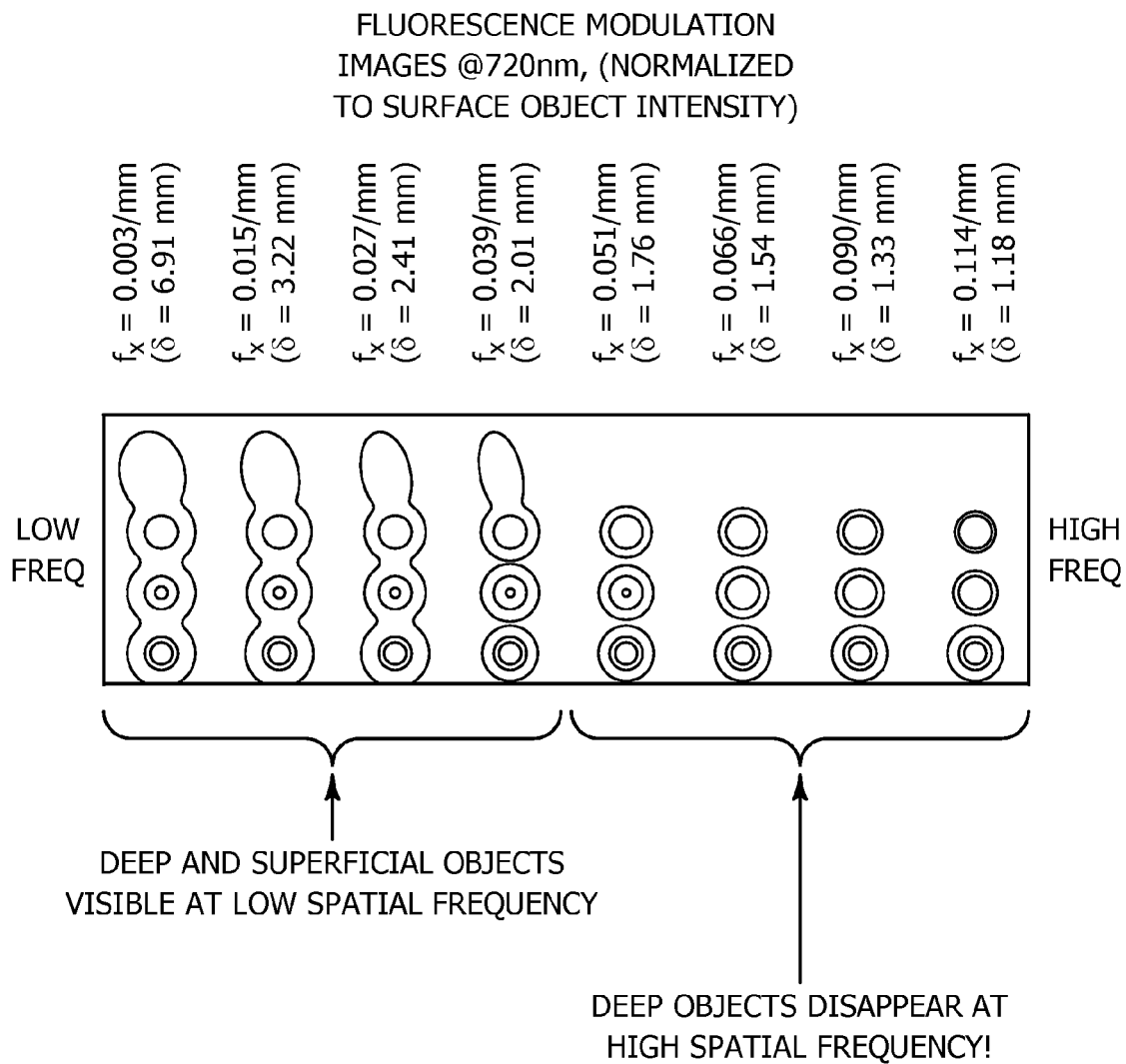
FIG. 8 is a fluorescence modulation images at 720 nm of the phantom of FIG. 6, which are normalized to surface object intensity for eight modulation images equally spaced in frequency.

Fluorescence modulation images at 720 nm, which are normalized to surface object intensity as shown in FIG. 8. Plotted here are eight, equally spaced in frequency, modulation images calculated at 720 nm. Note that when going from a low to high modulation frequency, the fluorescence response drops off for deeper objects relative to superficial ones. This feature is brought out in this dataset by normalizing to the surface object intensity. Note also the apparent increase in spatial resolution at higher modulation frequencies, by the sharpening up of deep, embedded objects. This is also apparent in other non-fluorescence data sets. In terms of image formation, a final image is a real-space convolution of the illumination and object functions. Normally planar illumination with very low spatial frequency moments is performed in biological imaging, limiting the final resolution from the start, and putting the image resolution burden entirely on the detection side. Here, high frequency illumination allows 'sharpening' of a turbid sample image as it provides a larger basis set for image reconstruction. Ranging in frequency space should allow for higher spatial resolution constructions in turbid media than was previously achievable.

Consider now a preliminary in-vivo fluorescence experiment using Cy5.5-labeled wound-targeting peptide. We imaged the abdominal view of a mouse three weeks following a permanent ligation of the left coronary artery, and four hours following administration of a fluorescent label which was believed to be localized in the areas of injury as well as systemic clearing by the bladder, liver and kidneys. The scar 26 formed over the chest area is clear in the DC reflectance image of FIG. 9.

Figure 9:
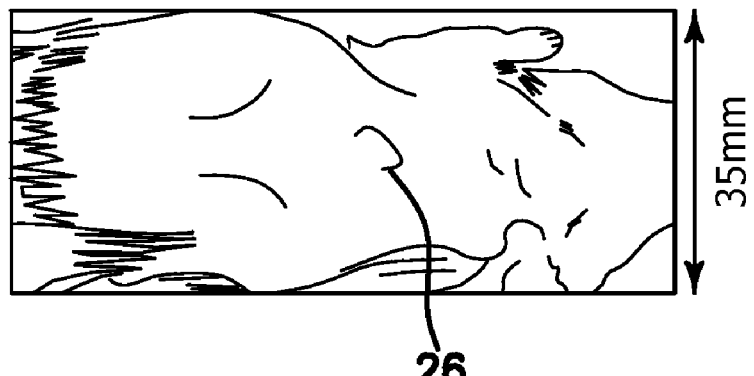
FIG. 9 is a DC reflectance image of the abdomen of a mouse in which a chest/heart scar has been surgically created.
Figure 10:
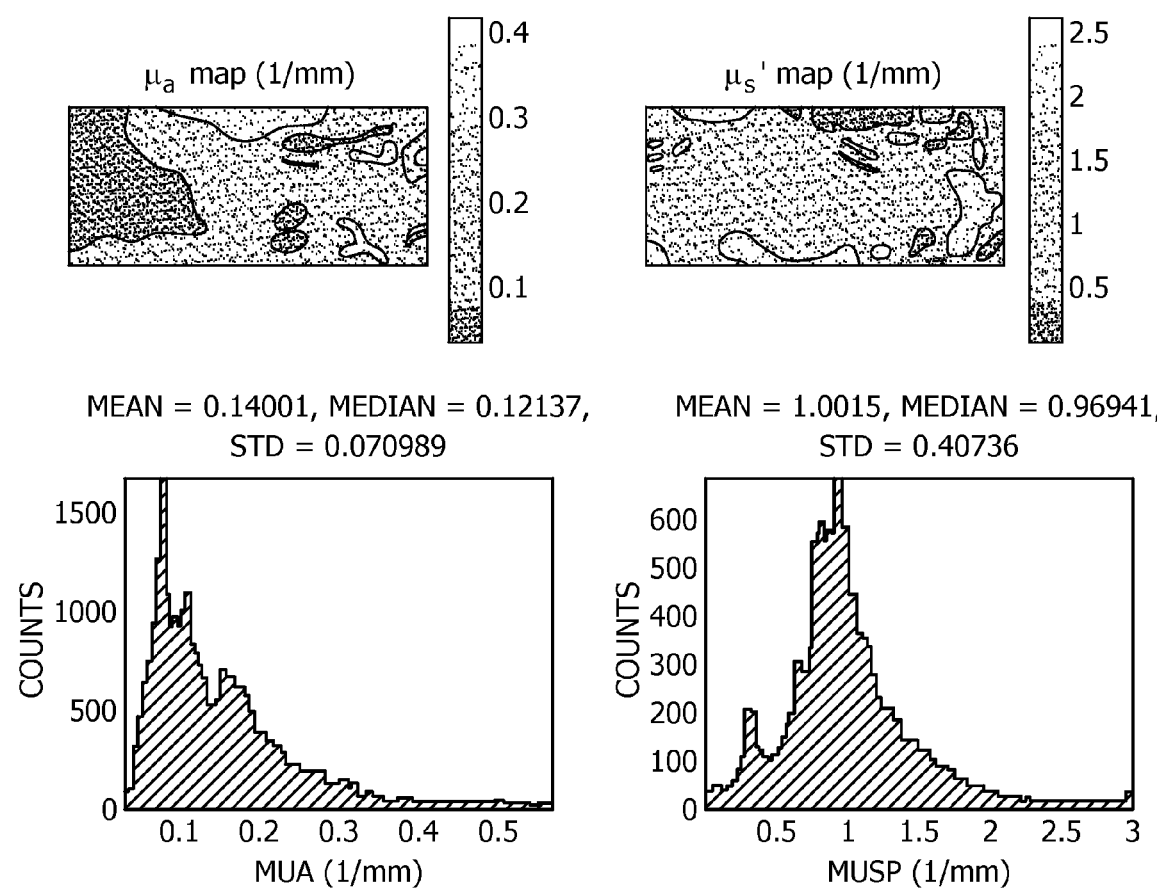
FIG. 10 shows in the upper portion excitation optical property maps ($\mu_a$ and $\mu_{s'}$ maps at 660 nm) of the mouse of FIG. 9. Corresponding quantitative histograms of the $\mu_a$ and $\mu_{s'}$ maps are shown in the lower portion of FIG. 10.

Excitation optical property maps ($\mu_a$ and $\mu_s'$ maps at 660 nm) of the mouse of FIG. 9 are shown in the upper portion of FIG. 10. Corresponding quantitative histograms of the $\mu_a$ and $\mu_s'$ maps are shown in the lower portion of FIG. 10. Among the interesting features in the optical property maps of the mouse is the apparent decrease in reduced scattering over areas of bone and cartilage. Note in particular the darkening in the hip region. There are some anomalies underneath the arm due to extreme curvature with respect to the camera. This anomaly can be corrected for if the topology is known, which is achievable through further analysis of the structured light reflectance.

Figure 11:
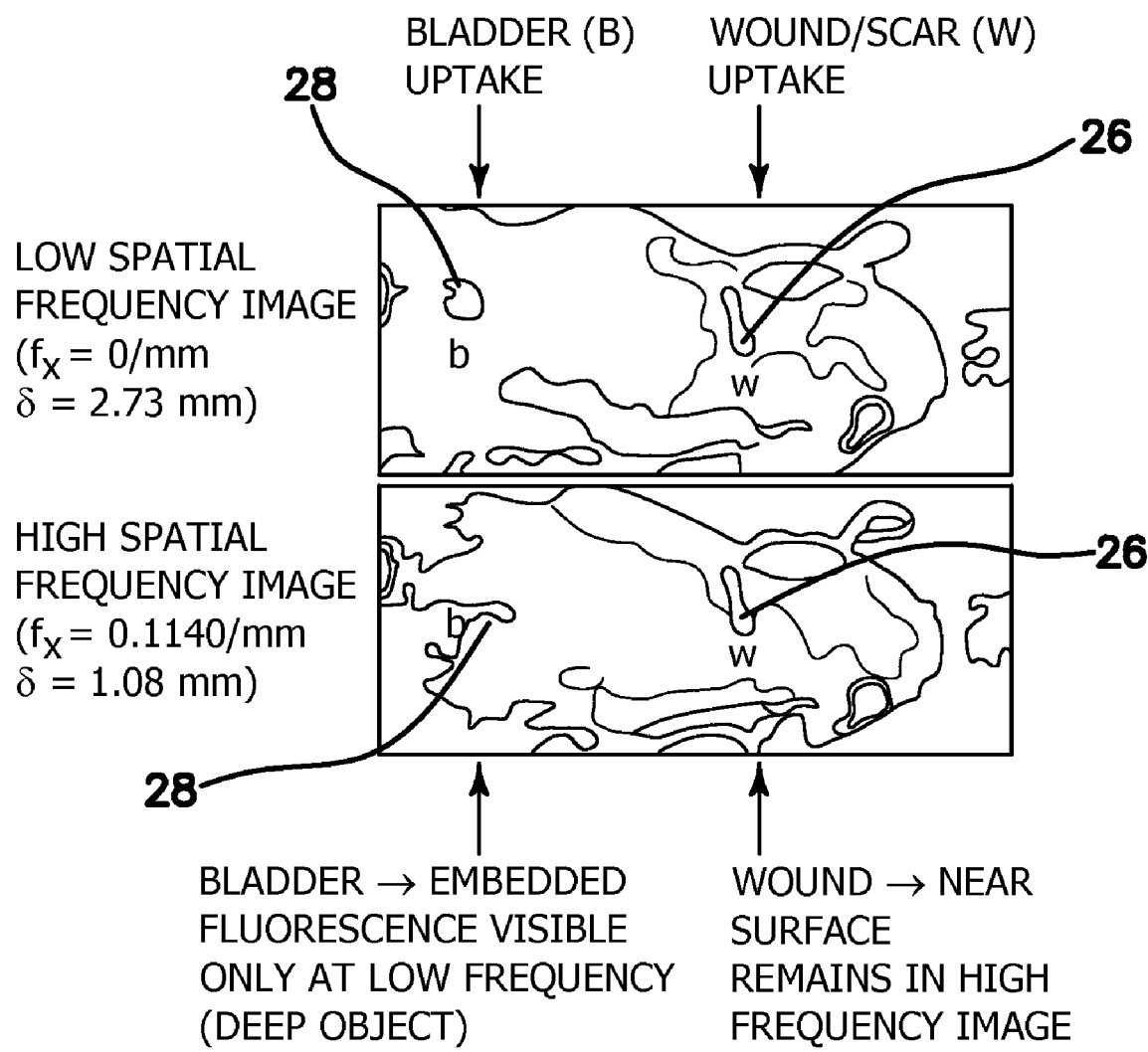
FIG. 11 shows two normalized fluorescence (F/R) modulation images of the mouse of FIG. 9 at 720 nm. The upper image is at a spatial modulation of 0/mm and the lower image is at a spatial modulation of 0.1140/mm.

Normalized fluorescence (F/R) modulation images of the mouse of FIG. 9 at 720 nm is shown in FIG. 11. The fluorescence images were divided, on a pixel-by-pixel basis, by the reflectance, as this was shown previously to provide stable, reproducible, and quantitative results. In practice, this also provides a nice flat-fielding, as the reflectance and fluorescence should have similar 'reflection coefficients' as a function of the surface angle. Note the change in normalized fluorescence signals from low to high frequencies. While, in the low frequency image both the bladder 28 and scar 26 are apparent, the high frequency image reveals only the scar 26. The scar 26 should run from the surface to the heart, at least 2 mm deep. The bladder 28, however, is imbedded in the peretoneal cavity, and therefore should have no signal at high frequency (shallow interrogation).

Quantitative functional tomography of absorption, scattering and fluorescence optical properties have thus been demonstrated above. In is expressly contemplated as being within the scope of the invention that hyperspectral techniques can also be added to the imaging modality. In particular, we are interested in studying the wavelength dependent absorption (melanin, hb, hbo2, h20, exogenous absorbers), scattering (cell structure, burn depth, bulk tissue/matrix organization) and fluorescence (EEM generation, quantitative measurement of dye concentration/affinities/binding), analogous to what has been done in frequency domain photon migration. The modulated light source adds an important degree of freedom to such a system, allowing for much of the spatial separation/3D imaging burden to be handled mostly by the illumination spatial frequency, and allowing spectral information to assist in determination of the functional quantitative values.

In conclusion, we demonstrate a rapid and economical procedure to achieve depth sectioning and quantitative optical property determination in turbid media over a wide three dimensional field-of-view. This technique will fill the gap between sub-millimeter imaging techniques such as used in confocal/multi-photon microscopy, or optical coherent tomography OCT and diffuse optical tomography.

Figure 15:
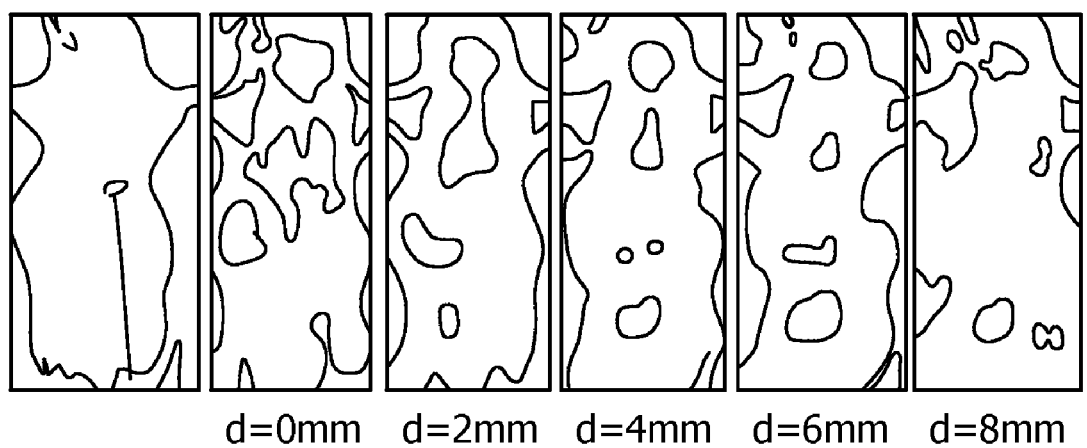
FIG. 15 is a series of six photographs of exogenous fluorescence contrast measurements in an in-vivo mouse model. Planar fluorescence is shown in the left most photograph and whole-body (50×20×2 mm) optical sections at 2 mm section depths from 0 to 8 mm appear immediately to the right. These sectional photographs demonstrate tomography of depth-resolved fluorescent structures in vivo.

FIG. 15 is a clear demonstration of in-vivo fluorescence sectioning and tomographic capabilities of modulated imaging. While the fundamental concept is identical to that described in connection with FIGS. 9 and 10, but the dataset of FIG. 15 has undergone depth-sectioning processing to visualize individual slices of contrast through the animal. This directly shows tomographic slices.

Modulation imaging (MI) allows depth ranging of the input modulated intensity wave with spatial frequency. This consequently allows control of the depth-dependence of fluorescence excited by this wave as well. This demonstrates this capability in an in-vivo mouse model, demonstrating that modulation imaging can perform diffuse optical tomography of exogenous fluorescence contrast in an in-vivo setting. In one experiment, fluorescently-labeled Annexin-5 was injected intravenously following 30 minutes of induced cardiac ischemia. Fluorescence is then measured with modulation imaging over the whole body using the same spatial frequencies as the previous experiment. Total measurement time was approximately 30 minutes, and could have been improved with a more sensitive intensified charge-coupled device (ICCD) detector. Planar fluorescence of the animal is shown in the leftmost photograph in FIG. 15. Reconstructed data is presented in the photographs to the right in FIG. 15 with whole-body (50×20×2 mm) optical sections shown from left to right, moving in approximately 2 mm-thick sections from top (depth=0 mm) to bottom (depth=8 mm) in the mouse. The depth-dependent fluorescence contrast is clear, with the disappearance of the stomach and lung fluorescence with depth, and simultaneous appearance of the bladder. While these images only probe down to 1 cm beneath the surface, increased sensitivity and dynamic range of the imaging system should deliver fluorescence contrast up to 2-3 cm deep in reflectance mode, and 4-5 cm deep in transmission mode.

Consider now the embodiment of the invention which illustrates its use for quantitative tomography, and a demonstration of high-resolution imaging at depth in both simulations, real measurements and reconstructions. Here, we present a diffraction tomography framework for high-resolution tomographic reconstruction in turbid media. First consider a simple case of a purely absorbing inclusion in a thin slice at a given depth beneath a surface of a mathematical model. We have modeled a 1.5 mm diameter object placed 4 mm beneath the surface. We have also acquired real diffuse reflectance data in a turbid system, designed to mirror the simulation geometry identically. For this we used a 10-micron layer of transparent mylar with an absorbing dot 1.5 mm±0.1 mm in diameter, submerged in a 1% intralipid solution at a depth of 4 mm. Measurements at 660 nm were taken at 42 spatial frequencies between 0 and 0.5/mm.

Figure 16:
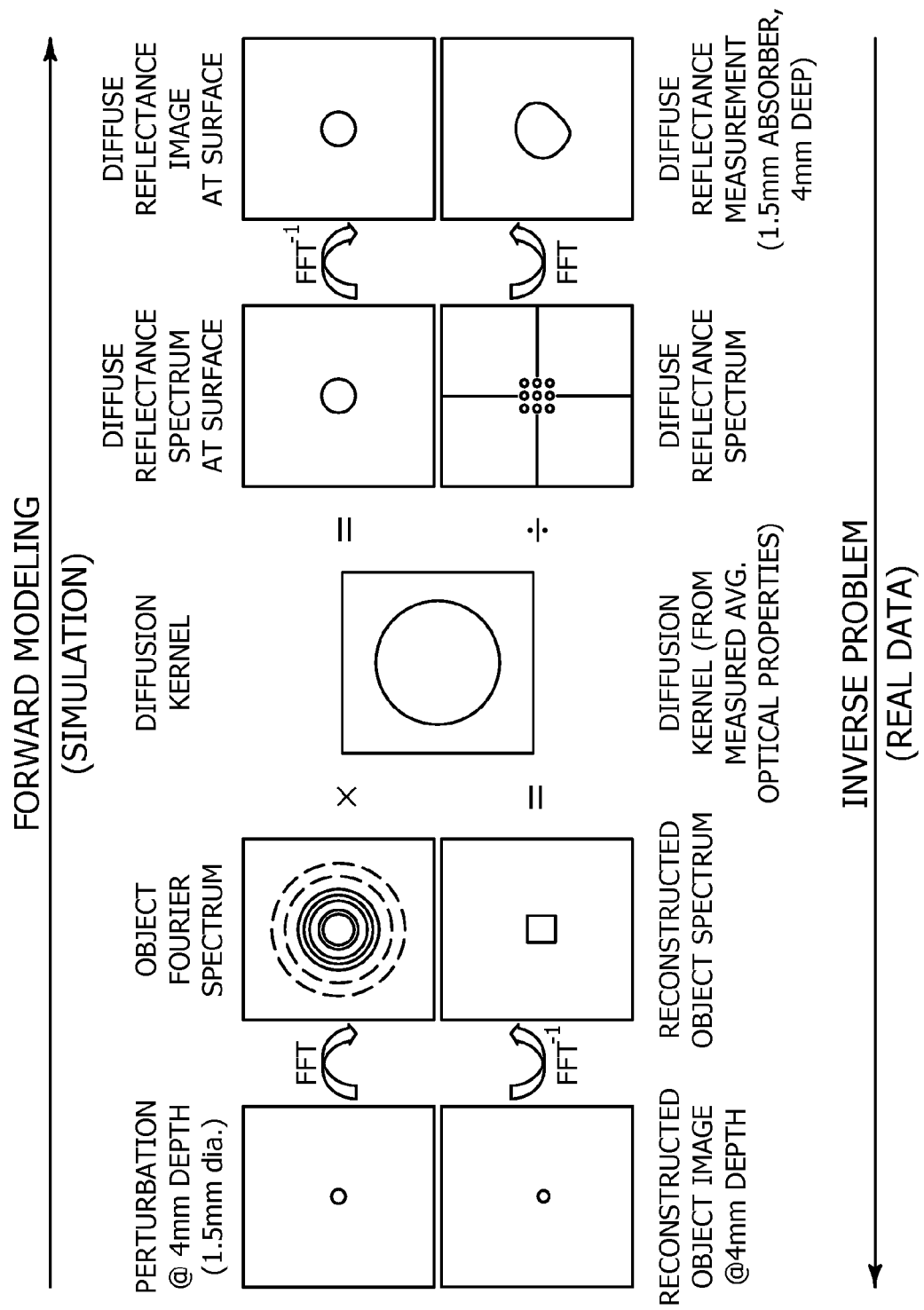
FIG. 16 is a diagram illustrated a diffraction tomography framework for planar imaging. From the top of the drawing starting on the left and going to the right a forward Fourier transform modeling of a 1.5 mm diameter absorbing perturbation at 4 mm depth in scattering media with a 30×30 mm field of view is illustrated. Form the bottom of the drawing starting on the right and going to the left an inverse Fourier problem of reconstruction of a measured 1.5 mm absorbing perturbation over a 30×30 mm field of view, submerged in 1% Intralipid at a depth of 4 mm is illustrated. Spectral windowing is used to limit the effect of high-frequency noise.

FIG. 16 is a diagram which shows the results of the use of a forward (top) and inverse (bottom) Fourier transform of a 1.5 mm diameter simulated and measured perturbations, respectively. On the top left portion of the drawing, the simulated perturbation at 4 mm depth is plotted over a 30×30 mm field of view. To view the object's Fourier spectral content as shown in the depiction to the immediate right, we apply a two dimensional Fast Fourier Transform (FFT). Just as high spatial frequencies of illumination are damped as they pass into the sample, high object spatial frequencies are damped equivalently as they propagate to the surface, where the diffusion damping kernel as shown in the center portion of the drawing is widely accepted, and proportional to the second (homogeneous) term of Equation 7. A final inverse transform yields the object perturbation as seen at the surface.

Proceeding in reverse order, on the bottom going from right to left in the drawing, we show the measurement of the diffuse reflectance at a single illumination frequency (0/mm) and perform a two dimensional FFT to view the diffuse perturbation spectrum. To deconvolve the effect of diffusion, we then divide by the diffusion kernel using optical properties determined from multi-frequency optical property measurements of the background, and a-priori knowledge of the object depth. We perform spectral windowing to avoid amplification of noise at high frequency as shown in the next depiction to the left, and finally inverse transform to recover a high-resolution image of the perturbation.

Figure 17:
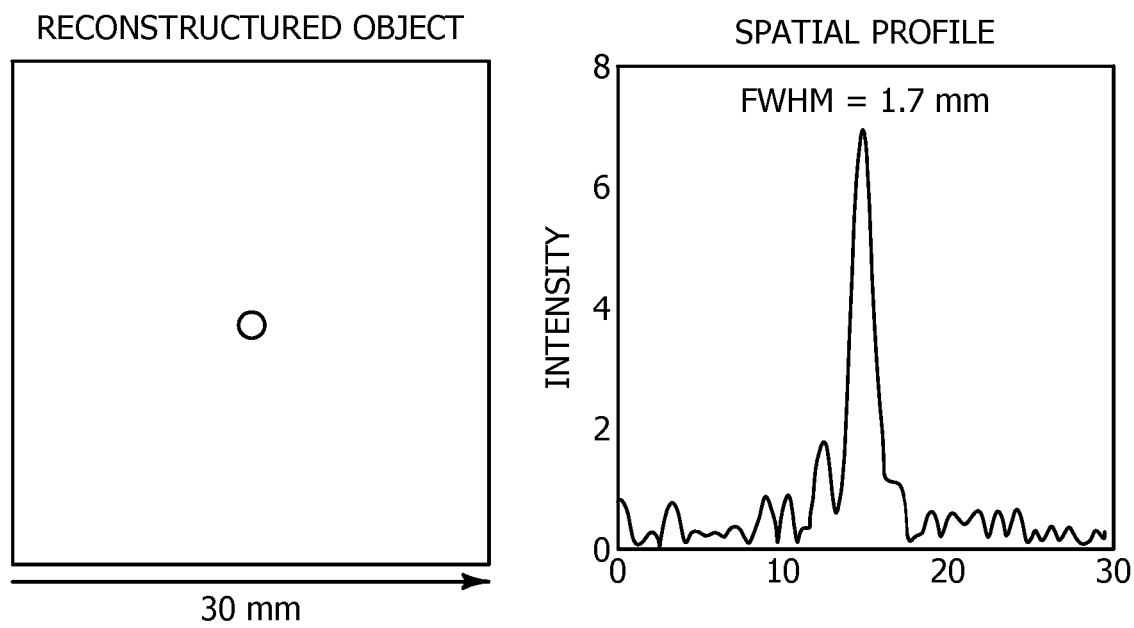
FIG. 17 is a photograph on the left showing an absorbing object at 4 mm depth, reconstructed from measured diffuse reflectance. On the right of the drawing is a graph of the corresponding spatial profile indicating high resolution and spatial accuracy, measuring a full-width at half maximum of 1.7 mm compared to the known 1.5 mm object diameter.
Figure 18:
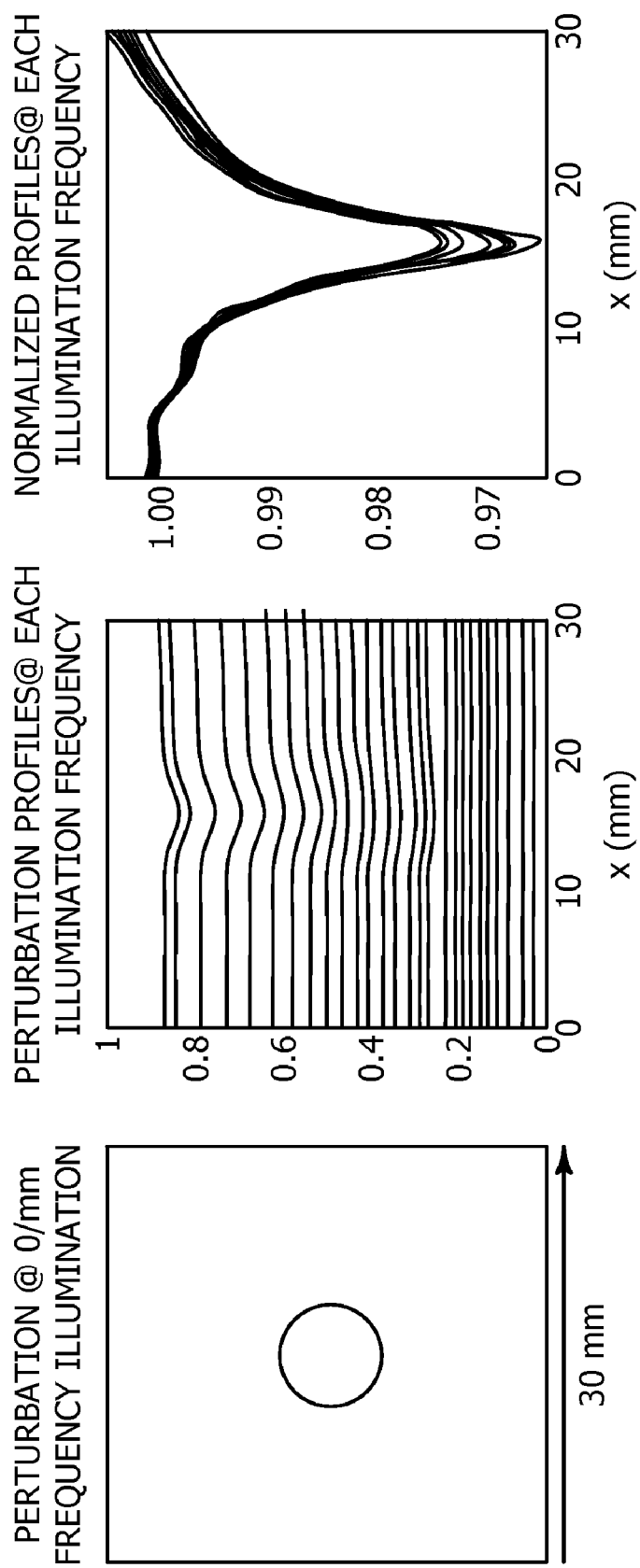
FIG. 18 shows on the leftmost depiction portion a photograph of an absorbing object at 4 mm depth, reconstructed from measured diffuse reflectance. In the center portion of the drawing is a graph showing the corresponding spatial profile at each illumination frequency. At the right most portion of the drawing is a graph of the corresponding normalized spatial profile indicating high resolution and spatial accuracy, measuring a full-width at half maximum of 1.7 mm compared to the known 1.5 mm object diameter.
Figure 19:
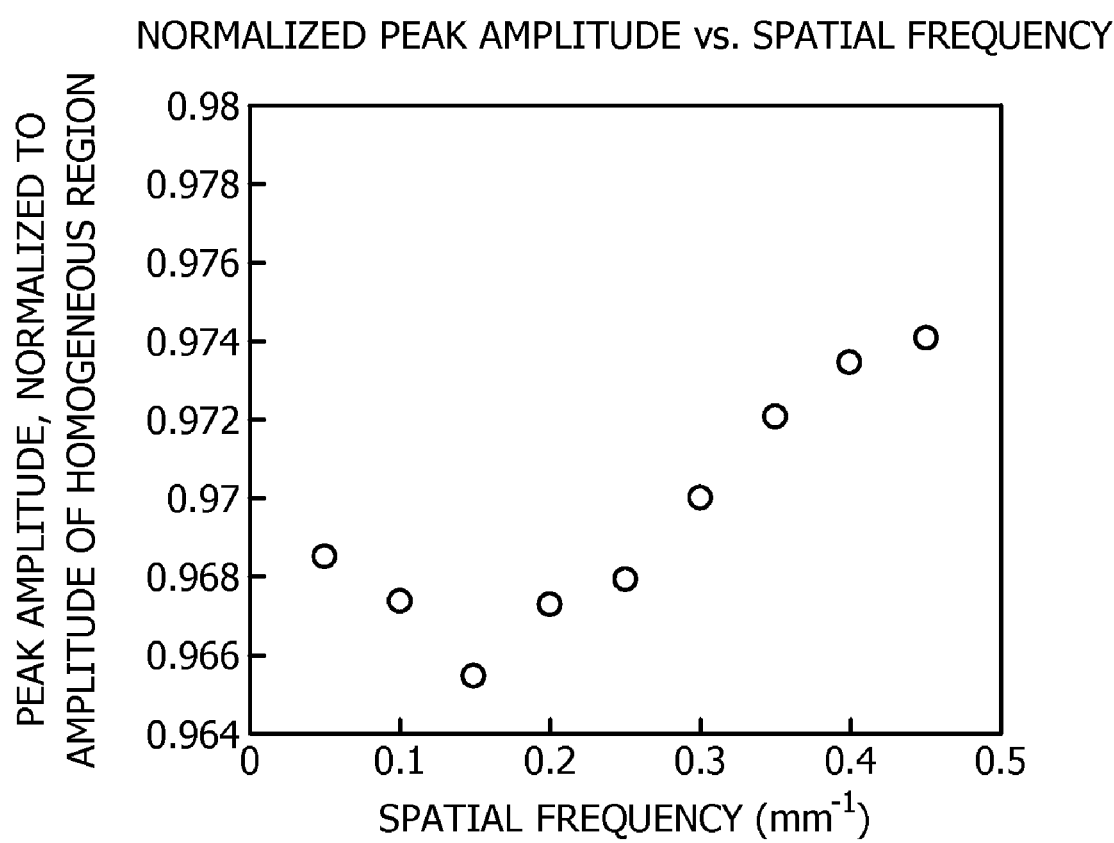
FIG. 19 is a graph of the amplitude perturbation of object at 4 mm depth as a function of spatial frequency, obtained from measured diffuse reflectance, indicating a changing depth profile of the background fluence. This differential sensitivity of interaction with the object demonstrates the possibility of quantitative tomography of object size, depth, and optical properties (fluorescence, absorption, or scattering) through use of forward models such as modeled by the equation, $$\varphi_0(z) = 3P_0 \left(\frac{\mu_s'}{\mu_{tr}}\right)\left(\frac{\mu_{eff}'^2}{\mu_{tr}^2} - 1\right)^{-1} \exp(-\mu_{tr}z) + C\exp(-\mu_{eff}'z),$$

In FIG. 17 the reconstructed object FWHM shows quantitative agreement with the known object size. In FIG. 18, we plot diffuse reflectance profiles for all 42 recovered spatial illumination frequencies and show changes in sensitivity to the 4 mm-deep object as spatial frequency increases. This behavior is due to the modification of the fluence profile which is predicted analytically by Equation 7. Further illustrating this effect, in FIG. 19 we plot the peak amplitude perturbation of the object at 4 mm depth as a function of spatial frequency, indicating a changing depth profile of the background fluence. This differential sensitivity of interaction with the object demonstrates the possibility to simultaneously recover quantitative optical property (fluorescence, absorption, or scattering) data spatially (x-y) and with depth (z), through the use of forward models such as Equation 7, and tomographic inversion techniques such as least-squares regression or pseudoinverse linear matrix multiplication.

Lastly, while we formulate these concepts within a diffusion context, they are qualitatively retained in more accurate solutions to the full radiative transport equation, such as in stochastic Monte Carlo simulations or direct numerical solutions, which extend light transport reconstruction models to low scattering, high absorption, and/or high spatial frequency regimes. Thus it can be appreciated that the invention contemplates generalized "depth-ranging" of "down-stream" light-dependent phenomena, including but not limited to fluorescence, depth-controlled light therapy dosimetry, depth-controlled thermal effects. These concepts have real-world implications in terms of existing businesses, including the Fraxel technology in cosmetic therapy.

Applications of various embodiments of the invention include, but are not limited to, medical diagnostics and therapeutic monitoring within a variety of tissues, and small animal imaging of fluorescence. In all biological studies, this technique provides the ability to resolve in depth tissue auto fluorescence from other exogenous fluorophores or the expression of genetically engineered protein fluorescence within the tissue.

It can now be appreciated that the invention is broadly directed to a method and apparatus exploiting the depth-selectivity/depth-sensitivity of the interaction of spatially modulated light with a turbid medium, or more particularly exploiting the modification of depth profile of light fluence rate through choice of spatial frequency of the incident light. The general behavior of this interaction with matter or the turbid medium is demonstrated for the first time in an analytic equation in this disclosure, which has illustrated one possible solution. The interaction which is exploited is clearly demonstrated in controlled phantom measurements shown in FIGS. 18 and 19.

The subsequent control of "down-stream" effects of this depth profile of the interaction of light with the turbid medium, includes but not limited to creating: a fluorescence profile such as demonstrated in phantom, and in-vivo in this disclosure; thermal profile in the turbid medium; and an acoustic profile or medium pressure waves in the turbid medium at any frequency and not limited only to the audible frequencies. Any secondary effect caused by the interaction of light with the matter of the turbid medium can be employed for any purpose such as imaging, therapeutic treatment or diagnostic examination.

The invention is also characterized by the use of an inversion algorithm to provide qualitative or quantitative high-resolution three dimensional representations of the absorption, scattering, fluorescence or other parameters indicative of the interaction of light with the turbid medium, which algorithm accounts for lateral diffusion as included in the use of calculated average optical properties described below as illustrated in FIGS. 17 and 18 and accounts for the depth-sensitivity discussed above.

The invention uses a calculated average of optical properties as a critical basis for accurate, high-resolution reconstruction of data or images. The high-resolution reconstruction of FIG. 17 would be impossible without accurate knowledge of the average background properties. This is a distinguishing capability of the illustrated embodiment of the invention which is particularly novel when combined with subsequent control of "down-stream" effects or use of an inversion algorithm as described above.

Thus, the invention can be characterized as a method and apparatus which exploits the interaction of light with matter to create secondary effects in the turbid medium as a function of depth in the turbid medium. The secondary effects are manipulated to provide a high resolution image of the turbid medium at a selected depth, to provide therapeutic mediation at a selected depth, or to provide diagnostic information at a selected depth.

In addition to wide field imaging, our approach can provide, but is not limited to, the following applications:
  a. Subsurface imaging/tomography: depth sensitivity to be assessed as a function of source spatial frequency, wavelength selection and/or amplitude modulation.
  b. Optical properties determination over large surface
  c. Quantitative reflectance, transmission and fluorescence imaging: For typical biological samples, measurement of quantitative fluorescence is confounded by the effects of scattering and absorption. The method disclosed here can provide both spatially resolved scattering and absorption properties in addition to fluorescence data. Hence, with the appropriate model of light propagation, one can deconvolve the effects of scattering and absorption from fluorophore spectra.
  d. Separation of the average background optical properties from the heterogeneity components from a single image
  e. Separation of background fluorescence from target fluorescence based on selection of spatial frequency of illumination.
  f. Separation of superficial fluorescent features from deep fluorescent features based on selection of spatial frequency of illumination.
  g. The utility of the invention includes, but is not limited to:
  h. Small animal imaging
  i. Pre-cancer and cancer detection and monitoring
    i. Fluorescence Endoscopy
    ii. Fluorescence Bronchosopy
    iii. Fluorescence Colposcopy (cervical cancer)
    iv. Intraoperative guidance for distinguishing between tissue types
    v. Moh's surgery guidance: delineation of skin tumor margin based on fluorescence and/or reflectance
    vi. Brain tumor resection: delineation of tumor margin based on fluorescence and/or reflectance
  j. Monitoring the efficacy of therapeutics—this includes drug development
  k. Monitoring age, disease related changes, and cosmetic agents in skin
    i. Wide field tissue hydration
    ii. Photoaging and response of photoaged skin to therapy (chemical, laser, Radiofrequency or ablation)
    iii. Quantification of the effectiveness of sunscreens (examination of both the sunscreen proper and physiologic response to radiation under different sunscreen formulations)
  l. Diabetes related changes in tissue status (for example, fluorescence changes related to advanced glycation end products)
  m. Burn severity/Burn Depth Assessment (important for grafting)
  n. Photodynamic therapy dosimetry
  o. Wide field tissue oximetry (useful for burn assessment, peripheral vascular disease diagnosis and management, neonatal oximetry)
  p. Chemical imaging (fluorescence, reflectance or combination) as means of quality control (Pharmaceuticals) and quantitative process engineering.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for quantitative modulated fluorescence imaging in the spatial frequency domain to perform depth sectioned fluorescence and reflectance imaging in a turbid medium comprising:
    exposing the turbid medium to a periodic pattern of illumination characterized by a spatial frequency with at least three spatially phase shifted periodic patterns of illumination;
    receiving the data image from the turbid medium;
    selecting a region of interest of the turbid medium;
    transforming the data image of the selected region of interest of the turbid medium;
    spatially filtering the transformed data image of the selected region of interest of the turbid medium; and
    reconstructing the spatially filtered transformed data image of the selected region of interest of the turbid medium;
    where exposing the turbid medium to a periodic pattern of illumination includes encoding the periodic pattern of illumination with at least three spatially phase shifted periodic patterns of illumination with a fluorescent excitation wavelength when exposing the turbid medium to the periodic pattern to provide depth-resolved discrimination of fluorescent structures within the turbid medium;
    where reconstructing the filtered transformed data image includes reconstructing a non-contact three dimensional image of spatially AC modulated remitted fluorescence within the turbid medium from the at least three spatially phase shifted periodic patterns of illumination.

2. The method of claim 1 where the steps of encoding and reconstructing provides spatially resolved optical properties at the excitation and emission wavelengths of interest, and further comprising deconvolving the effects of scattering and absorption from the measured fluorescence.

3. The method of, claim 1 further comprising simultaneously mapping surface and subsurface media structure, media function and media composition using AC spatially modulated remitted fluorescence within the turbid medium.

4. The method of claim 3 where simultaneously mapping surface and subsurface media structure, function and composition comprises assessing depth sensitivity as a function of wavelength selection and/or amplitude modulation.

5. The method of claim 1 further comprising wide field imaging using AC modulated remitted fluorescence within the turbid medium.

6. The method of claim 1 further comprising separating the average background optical properties from heterogeneity components from a single image.

7. The method of claim 6 further comprising separating background fluorescence from target fluorescence based on selection of spatial frequency of illumination, and separating superficial fluorescent features from deep fluorescent features based on selection of spatial frequency of illumination.

8. The method of claim 1 further comprising separating superficial fluorescent features from deep fluorescent features based on selection of spatial frequency of illumination.

9. The method of claim 1 further comprising extracting qualitative and quantitative structure, function and composition information of fluorophores in the turbid media from spatially encoded data.

10. The method of claim 9 where extracting qualitative and quantitative structure, function and composition information from spatially encoded data comprises quantitatively measuring fluorescence by both spatially resolving scattering and absorption properties in addition to fluorescence data and deconvolving the effects of scattering and absorption from fluorophore spectra.

11. The method of claim 1 further comprising resolving in depth tissue auto fluorescence from other exogenous fluorophores or the expression of genetically engineered protein fluorescence within the tissue using selection of spatial frequency of illumination.

12. The method of claim 11 further comprising assessing depth sensitivity as a function of wavelength selection and/or amplitude modulation.

13. An apparatus for quantitative spatially modulated fluorescence imaging to perform depth sectioned fluorescence and reflectance imaging of a turbid sample composed of a fluorescent turbid medium comprising:
    a source to expose a turbid sample to a spatially modulated periodic pattern of illumination, where the source provides at least three spatially phase shifted periodic patterns of illumination encoded with a fluorescent excitation wavelength to provide depth-resolved discrimination of fluorescent structures within the turbid medium;
    a camera to receive the data image from the sample;
    a signal processor configured to Fourier transform the data image of the sample, to spatially filter the transformed data image of the sample, and to reconstruct the spatially filtered transformed data image of the sample, where reconstructing the filtered transformed data image includes reconstructing a non-contact three dimensional image of fluorescence at an emission frequency within the turbid sample from a spatially AC modulated remitted fluorescence.

14. The apparatus of claim 13 where the source and means for reconstructing in combination determine spatially resolved optical properties at the excitation and emission wavelengths of interest, and the means for reconstructing further deconvolving the effects of scattering and absorption from the measured fluorescence.

15. The apparatus of claim 13 where the means for reconstructing further simultaneously maps surface and subsurface media structure, function and composition.

16. The apparatus of claim 15 where the means for reconstructing assesses depth sensitivity as a function of source spatial frequency, wavelength selection and/or amplitude modulation.

17. The apparatus of claim 13 where the source and means for reconstructing in combination perform wide field imaging.

18. The apparatus of claim 17 where the means for reconstructing spatially resolves optical properties determination over a large area.

19. The apparatus of claim 13 where the means for reconstructing separates the average background optical properties from heterogeneity components from a single image.

20. The apparatus of claim 19 where the means for reconstructing separates background fluorescence from target fluorescence based on selection of spatial frequency of illumination, and separates superficial fluorescent features from deep fluorescent features based on selection of spatial frequency of illumination.

21. The apparatus of claim 13 where the means for reconstructing separates superficial fluorescent features from deep fluorescent features based on selection of spatial frequency of illumination.

22. The apparatus of claim 13 where the means for reconstructing extracts qualitative and quantitative structure, function and composition information from spatially encoded data.

23. The apparatus of claim 22 where the means for reconstructing quantitatively measures fluorescence by both spatially resolving scattering and absorption properties in addition to fluorescence data and deconvolving the effects of scattering and absorption from fluorophore spectra.

24. The apparatus of claim 13 where the means for reconstructing resolves in depth tissue auto fluorescence from other exogenous fluorophores or the expression of genetically engineered protein fluorescence within the tissue.

25. The apparatus of claim 13 where the means for reconstructing assesses depth sensitivity as a function of source spatial frequency, wavelength selection and/or amplitude modulation.

26. The apparatus of claim 13 where the means for reconstructing separates superficial fluorescent features from deep fluorescent features based on selection of spatial frequency of illumination.

* * * * *